United States Patent
Dyballa et al.

(10) Patent No.: US 9,605,010 B2
(45) Date of Patent: Mar. 28, 2017

(54) MONOPHOSPHITE COMPOUNDS HAVING A METHYL GROUP

(71) Applicant: EVONIK DEGUSSA GMBH, Essen (DE)

(72) Inventors: Katrin Marie Dyballa, Recklinghausen (DE); Robert Franke, Marl (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/141,069

(22) Filed: Apr. 28, 2016

(65) Prior Publication Data

US 2016/0318959 A1   Nov. 3, 2016

(30) Foreign Application Priority Data

Apr. 29, 2015 (DE) .................... 10 2015 207 860

(51) Int. Cl.

| | | |
|---|---|---|
| *C07F 15/00* | (2006.01) | |
| *C07C 45/50* | (2006.01) | |
| *B01J 31/18* | (2006.01) | |
| *C07F 9/6574* | (2006.01) | |
| *B01J 31/22* | (2006.01) | |
| *C07F 9/145* | (2006.01) | |

(52) U.S. Cl.
CPC ......... *C07F 9/65744* (2013.01); *B01J 31/185* (2013.01); *B01J 31/22* (2013.01); *C07C 45/50* (2013.01); *C07F 9/145* (2013.01); *C07F 15/008* (2013.01); *B01J 2231/321* (2013.01); *B01J 2531/821* (2013.01)

(58) Field of Classification Search
CPC .... C07F 15/008; C07F 9/65744; C07C 45/50; B01J 31/185
USPC ....................................... 556/13; 568/12, 13
See application file for complete search history.

(56) References Cited

U.S. PATENT DOCUMENTS

| | | | |
|---|---|---|---|
| 6,653,485 B2 * | 11/2003 | Zhang ................ | B01J 31/1875 546/22 |
| 8,003,816 B2 | 8/2011 | Selent et al. | |
| 9,212,195 B1 | 12/2015 | Dyballa et al. | |
| 9,221,850 B2 | 12/2015 | Dyballa et al. | |
| 9,290,527 B2 | 3/2016 | Fridag et al. | |
| 2003/0144559 A1 | 7/2003 | Hess et al. | |

FOREIGN PATENT DOCUMENTS

| | | |
|---|---|---|
| DE | 19954721 A1 | 5/2001 |
| DE | 102006058682 | 6/2008 |
| DE | 102008043584 | 5/2010 |
| EP | 0155508 | 9/1985 |
| WO | 02/40491 A1 | 5/2002 |
| WO | 2015176928 | 11/2015 |

OTHER PUBLICATIONS

Extended European Search Report dated Sep. 12, 2016 received in EP Application No. 16165322.5 (9 pages).
Carrilho, Rui M. B. et al: "Rhodium/tris-binaphthyl chiral momophosphate complexes: Efficient catalysts for the hydroformylation of disubstituted arly olefins", Journal of Organometallic Chemistry, 698 (2012), (pp. 28-34).
Carrilho, Rui M. B. et al: "Asymmetric Hydrovinylation and Hydrogenation with Metal Complexes of $C_3$-Symmetric Tris-Binaphthyl Monophosphites", European Journal of Inorganic Chemistry (2014) (6), (pages 1034-1041).
Carrilho, Rui M. B. et al: "New binaphthyl-based $C_3$-Symmetric Chiral Hemlabile Momophosphite Ligands: Synthesis and Characterization of Their Platinum Complexes", Chemistry Letters, 38(8). (2009) (pp. 844-845).

* cited by examiner

*Primary Examiner* — Porfirio Nazario Gonzalez
(74) *Attorney, Agent, or Firm* — Smith, Gambrell & Russell, LLP

(57) ABSTRACT

Novel monophosphite compounds having a methyl group, and a process for preparing these compounds, which are especially suitable for use as ligands in hydroformylation reactions.

18 Claims, No Drawings

MONOPHOSPHITE COMPOUNDS HAVING A METHYL GROUP

The present invention relates to novel monophosphite compounds having a methyl group, and to a process for preparing these compounds, which are especially suitable for use as ligands in hydroformylation reactions. The invention additionally also relates to complexes including at least one of these monophosphite compounds and to the use of the aforementioned compounds and/or complexes in hydroformylation reactions.

The reactions between olefin compounds, carbon monoxide and hydrogen in the presence of a catalyst to give the aldehydes comprising one additional carbon atom are known as hydroformylation or oxo synthesis. In these reactions, compounds of the transition metals of group VIII of the Periodic Table of the Elements are frequently employed as catalysts. Known ligands are, for example, compounds from the classes of the phosphines, phosphites and phosphonites, each with trivalent phosphorus $P^{III}$.

A good overview of the state of the hydroformylation of olefins can be found in B. CORNILS, W. A. HERRMANN, "Applied Homogeneous Catalysis with Organometallic Compounds", vol. 1 & 2, VCH, Weinheim, N.Y., 1996 or R. Franke, D. Selent, A. BBrner, "Applied Hydroformylation", Chem. Rev., 2012, DOI:10.1021/cr3001803.

Every catalytically active composition has its specific benefits. According to the feedstock and target product, therefore, different catalytically active compositions are used.

The disadvantage of bi- and polydentate phosphine ligands is a relatively high level of complexity necessary for preparation thereof. It is therefore often unviable to use such systems in industrial processes. An additional factor is comparatively low activity, which has to be compensated for by chemical engineering, through high residence times. This in turn leads to unwanted side reactions of the products.

In Angew. Chem. Int. Ed. 2000, 39, No. 9, p. 1639-1641, Börner et al. describe ligands having one P—C bond and two P—O bonds; these are thus phosphonites. The phosphonites described therein, when used in hydroformylation, have n/iso selectivities (n/iso=the ratio of linear aldehyde (=n) to branched (=iso) aldehyde)) of 0.61 to 1.57.

The phosphonite ligands described in DE 199 54 721 A1 have a good n/iso selectivity. However, studies have shown that the compound II-c (in DE 199 54 721; page 6) has a tendency to a photochemically induced breakdown. Because of the instability of the compound, it cannot be stored, and for that reason the use of the compound as ligand in catalysis on the industrial scale is uneconomic. Therefore, the compound should not be used on the industrial scale.

A further disadvantage of ligands having a phosphonite structure is that their preparation is very complex. However, the possibility of a convenient and simple synthesis plays a fundamental role for the use of ligands in an industrial scale process, since the production costs for a ligand can only be so high that the viability of the overall process in which the ligand is later used is still assured.

Rhodium-monophosphite complexes in catalytically active compositions are suitable for the hydroformylation of branched olefins having internal double bonds.

EP 0 155 508 discloses the use of bisarylene-substituted monophosphites in the rhodium-catalysed hydroformylation of sterically hindered olefins, e.g. isobutene. Rhodium concentrations used here are sometimes very high (one being 250 ppm), which is uneconomic for an industrial scale process in view of the current cost of rhodium.

With respect to the known prior art, the problem addressed by the present invention is that of providing alternative ligands and complexes including them for use in hydroformylation reactions which do not have the disadvantages indicated in connection with the existing ligands. More particularly, the novel ligands are preferably to be synthesizable with a lower level of complexity and correspondingly also with lower costs than the ligands known from the prior art. Preferably, the novel ligands are also to be usable in industrial scale hydroformylation.

This object is achieved by compounds according to Claim 1. More particularly, the problem is solved by monophosphite compounds having or consisting of one of the two general structures I and II:

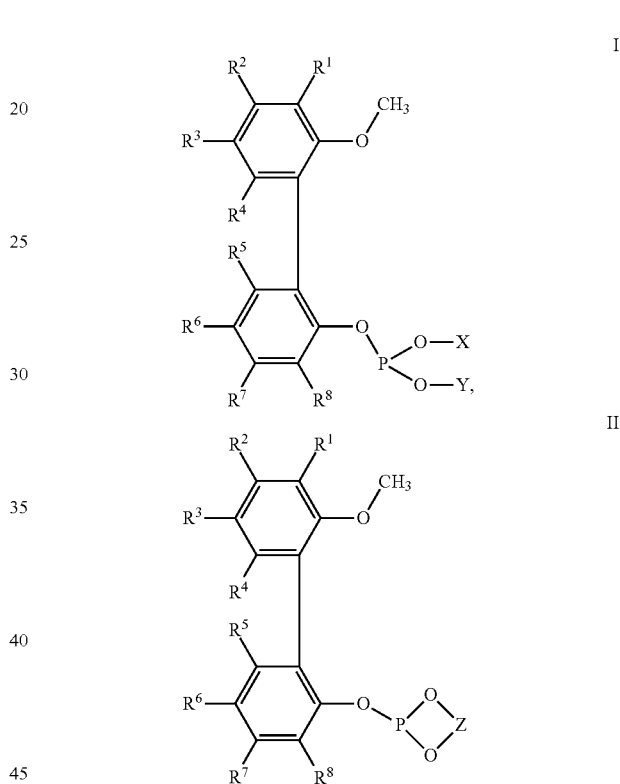

where $R^1$, $R^2$, $R^3$, $R^4$, $R^5$, $R^6$, $R^7$, $R^8$ are each independently selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —Cl, —F, —Br, —I, —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, —N[($C_1$-$C_{12}$)-alkyl]$_2$;
where X and Y are each independently selected from:
—($C_1$-$C_{12}$)-alkyl, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_1$-$C_{12}$)-alkyl-($C_6$-$C_{20}$)-aryl, —($C_6$-$C_{20}$)-aryl-COO—($C_1$-$C_{12}$)-alkyl, —($C_6$-$C_{20}$)-aryl-CONH—($C_1$-$C_{12}$)-alkyl, —($C_6$-$C_{20}$)-aryl-CON[($C_1$-$C_{12}$)-alkyl]$_2$, —($C_4$-$C_{20}$)-heteroaryl, —($C_4$-$C_{20}$)-heteroaryl-($C_1$-$C_{12}$)-alkyl, —($C_5$-$C_8$)-cycloalkyl, —($C_5$-$C_8$)-heterocycloalkyl, —($C_6$-$C_{20}$)-aryl-CO—($C_6$-$C_{20}$)-aryl;
and where Z is selected from:
—($C_1$-$C_{12}$)-alkyl, —($C_6$-$C_{20}$)-aryl, —($C_6$-$C_{20}$)-aryl-($C_1$-$C_{12}$)-alkyl, —($C_1$-$C_{12}$)-alkyl-O—($C_6$-$C_{20}$)-aryl, —($C_4$-

$C_{20}$)-heteroaryl-, —($C_6$-$C_{20}$)-aryl-CO—($C_6$-$C_{20}$)-aryl-, —($C_6$-$C_{20}$)-aryl-($C_6$-$C_{20}$)-aryl-.

($C_1$-$C_{12}$)-Alkyl and O—($C_1$-$C_{12}$)-alkyl may each be unsubstituted or substituted by one or more identical or different radicals selected from ($C_3$-$C_{12}$)-cycloalkyl, ($C_3$-$C_{12}$)-heterocycloalkyl, ($C_6$-$C_{20}$)-aryl, fluorine, chlorine, cyano, formyl, acyl and alkoxycarbonyl.

($C_3$-$C_{12}$)-Cycloalkyl and ($C_3$-$C_{12}$)-heterocycloalkyl may each be unsubstituted or substituted by one or more identical or different radicals selected from ($C_1$-$C_{12}$)-alkyl, ($C_1$-$C_{12}$)-alkoxy, ($C_3$-$C_{12}$)-cycloalkyl, ($C_3$-$C_{12}$)-heterocycloalkyl, ($C_6$-$C_{20}$)-aryl, fluorine, chlorine, cyano, formyl, acyl and alkoxycarbonyl.

($C_6$-$C_{20}$)-Aryl and —($C_6$-$C_{20}$)-aryl-($C_6$-$C_{20}$)-aryl- may each be unsubstituted or substituted by one or more identical or different radicals selected from:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, -halogen (such as Cl, F, Br, I), —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, —N[($C_1$-$C_{12}$)-alkyl]$_2$.

In the context of the invention, the expression "—($C_1$-$C_{12}$)-alkyl" encompasses straight-chain and branched alkyl groups. Preferably, these groups are unsubstituted straight-chain or branched —($C_1$-$C_8$)-alkyl groups and most preferably —($C_1$-$C_6$)-alkyl groups. Examples of ($C_1$-$C_{12}$)-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethyl propyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression "—($C_1$-$C_{12}$)-alkyl" also apply to the alkyl groups in —O—($C_1$-$C_{12}$)-alkyl, i.e. in —($C_1$-$C_{12}$)-alkoxy. Preferably, these groups are unsubstituted straight-chain or branched —($C_1$-$C_6$)-alkoxy groups.

Substituted —($C_1$-$C_{12}$)-alkyl groups and substituted —($C_1$-$C_{12}$)-alkoxy groups may have one or more substituents, depending on their chain length. The substituents are preferably each independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl and alkoxycarbonyl.

The expression "—($C_3$-$C_{12}$)-cycloalkyl", in the context of the present invention, encompasses mono-, bi- or tricyclic hydrocarbyl radicals having 3 to 12, especially 5 to 12, carbon atoms. These include cyclopropyl, cyclobutyl, cyclopentyl, cyclohexyl, cycloheptyl, cyclooctyl, cyclododecyl, cyclopentadecyl, norbornyl and adamantyl.

The expression "—($C_3$-$C_{12}$)-heterocycloalkyl groups", in the context of the present invention, encompasses nonaromatic saturated or partly unsaturated cycloaliphatic groups having 3 to 12, especially 5 to 12, carbon atoms. The —($C_3$-$C_{12}$)-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms are replaced by heteroatoms or heteroatom-containing groups. The heteroatoms or the heteroatom-containing groups are preferably selected from —O—, —S—, —N—, —N(=O)—, —C(=O)— and —S(=O)—. Examples of —($C_3$-$C_{12}$)-heterocycloalkyl groups are tetrahydrothiophenyl, tetrahydrofuryl, tetrahydropyranyl and dioxanyl.

Substituted —($C_3$-$C_{12}$)-cycloalkyl groups and substituted —($C_3$-$C_{12}$)-heterocycloalkyl groups may have one or more (e.g. 1, 2, 3, 4 or 5) further substituents, depending on their ring size. These substituents are preferably each independently selected from —($C_1$-$C_{12}$)-alkyl, —($C_1$-$C_{12}$)-alkoxy, —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl and alkoxycarbonyl. Substituted —($C_3$-$C_{12}$)-cycloalkyl groups preferably bear one or more —($C_1$-$C_6$)-alkyl groups. Substituted —($C_3$-$C_{12}$)-heterocycloalkyl groups preferably bear one or more —($C_1$-$C_6$)-alkyl groups.

In the context of the present invention, the expression "—($C_6$-$C_{20}$)-aryl and —($C_6$-$C_{20}$)-aryl-($C_6$-$C_{20}$)-aryl-" encompasses mono- or polycyclic aromatic hydrocarbyl radicals. These have 6 to 20 ring atoms, more preferably 6 to 14 ring atoms, especially 6 to 10 ring atoms. Aryl is preferably —($C_6$-$C_{10}$)-aryl and —($C_6$-$C_{10}$)-aryl-($C_6$-$C_{10}$)-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

Substituted —($C_6$-$C_{20}$)-aryl groups and —($C_6$-$C_{20}$)-aryl-($C_6$-$C_{20}$)-aryl groups may have one or more (e.g. 1, 2, 3, 4 or 5) substituents, depending on the ring size. These substituents are preferably each independently selected from —H, —($C_1$-$C_{12}$)-alkyl, —O—($C_1$-$C_{12}$)-alkyl, —O—($C_6$-$C_{20}$)-aryl, —($C_6$-$C_{20}$)-aryl, -halogen (such as Cl, F, Br, I), —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, —N[($C_1$-$C_{12}$)-alkyl]$_2$.

Substituted —($C_6$-$C_{20}$)-aryl groups and —($C_6$-$C_{20}$)-aryl-($C_6$-$C_{20}$)-aryl groups are preferably substituted —($C_6$-$C_{10}$)-aryl groups and —($C_6$-$C_{10}$)-aryl-($C_6$-$C_{10}$)-aryl groups, especially substituted phenyl or substituted naphthyl or substituted anthracenyl. Substituted —($C_6$-$C_{20}$)-aryl groups preferably bear one or more, for example 1, 2, 3, 4 or 5, substituents selected from —($C_1$-$C_{12}$)-alkyl groups, —($C_1$-$C_{12}$)-alkoxy groups.

Even though all aforementioned substituents are possible substituents for the radicals designated as $R^1$ to $R^8$ in the compounds of the formulae I and II, —H, —($C_1$-$C_{12}$)-alkyl, —O—($C_1$-$C_{12}$)-alkyl, —O—($C_6$-$C_{20}$)-aryl, —($C_6$-$C_{20}$)-aryl, —Cl, —F, —Br, —I, —COO—($C_1$-$C_{12}$)-alkyl, —CO—($C_1$-$C_{12}$)-alkyl, —CO—($C_6$-$C_{20}$)-aryl, —COOH, —OH, —SO$_3$H, —NO$_2$, —CN, —NH$_2$, —N[($C_1$-$C_{12}$)-alkyl]$_2$ are preferred substituents for $R^1$ to $R^8$. Especially preferred substituents for $R^1$ to $R^8$ are —H, —($C_1$-$C_{12}$)-alkyl, —O—($C_1$-$C_{12}$)-alkyl, —O—($C_6$-$C_{20}$)-aryl, —($C_6$-$C_{20}$)-aryl, —Cl, —F, —Br, —I, —OH, —NO$_2$, —NH$_2$.

In one embodiment, $R^1$ to $R^8$ are preferably —H, —($C_1$-$C_{12}$)-alkyl, —O—($C_1$-$C_{12}$)-alkyl, —O—($C_6$-$C_{20}$)-aryl, —($C_6$-$C_{20}$)-aryl, —Cl, —F, —Br, —I.

In one embodiment, $R^1$ to $R^8$ are preferably —H, —($C_1$-$C_{12}$)-alkyl, —O—($C_1$-$C_{12}$)-alkyl, —O—($C_6$-$C_{20}$)-aryl, —($C_6$-$C_{20}$)-aryl; particular preference among these being given to —H, —($C_1$-$C_{12}$)-alkyl and —O—($C_1$-$C_{12}$)-alkyl.

In one embodiment, $R^3$ and $R^6$ are each —O—($C_1$-$C_{12}$)-alkyl.

In one embodiment, $R^3$ and $R^6$ are each —OMe.

In one embodiment, $R^1$ and $R^8$ are each —($C_1$-$C_{12}$)-alkyl.

In one embodiment, $R^1$ and $R^8$ are each tert-butyl.

In one embodiment, $R^1$, $R^3$, $R^6$ and $R^8$ are each —($C_1$-$C_{12}$)-alkyl.

In one embodiment, $R^1$, $R^3$, $R^6$ and $R^8$ are each methyl.

In one embodiment, $R^1$, $R^3$, $R^6$ and $R^8$ are each tert-butyl.

In one embodiment, $R^1$, $R^2$, $R^3$, $R^4$, $R^5$, $R^6$, $R^7$ and $R^8$ are each —H.

Of the aforementioned X and Y substituents in compounds of formula I, especially preferred substituents are —$(C_1$-$C_{12})$-alkyl, —$(C_6$-$C_{20})$-aryl, —$(C_6$-$C_{20})$-aryl-$(C_1$-$C_{12})$-alkyl, —$(C_1$-$C_{12})$-alkyl-$(C_6$-$C_{20})$-aryl, —$(C_4$-$C_{20})$-heteroaryl and —$(C_5$-$C_8)$-cycloalkyl.

In one embodiment, X and Y are the same radicals.

Of the aforementioned possible substituents for Z in compounds of formula II, preferred substituents are —$(C_1$-$C_{12})$-alkyl-, —$(C_6$-$C_{20})$-aryl-, —$(C_6$-$C_{20})$-aryl-$(C_1$-$C_{12})$-alkyl-, —$(C_1$-$C_{12})$-alkyl-$(C_6$-$C_{20})$-aryl- and —$(C_6$-$C_{20})$-aryl-$(C_6$-$C_{20})$-aryl-. Particularly preferred Z substituents have at least one phenyl ring and preferably two or optionally more phenyl rings, where the phenyl rings are optionally substituted, especially by $(C_1$-$C_{12})$-alkyl radicals or by —O—$(C_1$-$C_{12})$-alkyl radicals.

In one embodiment, Z is:

In a further embodiment, Z is —$(C_6$-$C_{20})$-aryl-$(C_6$-$C_{20})$-aryl-.

In one embodiment, the compound has the general structure III:

III where $R^9$, $R^{10}$, $R^{11}$, $R^{12}$, $R^{13}$, $R^{14}$, $R^{15}$, $R^{16}$ are each independently selected from:

—H, —$(C_1$-$C_{12})$-alkyl, —O—$(C_1$-$C_{12})$-alkyl, —O—$(C_6$-$C_{20})$-aryl, —$(C_6$-$C_{20})$-aryl, -halogen (such as Cl, F, Br, I), —COO—$(C_1$-$C_{12})$-alkyl, —CONH—$(C_1$-$C_{12})$-alkyl, —$(C_6$-$C_{20})$-aryl-CON[$(C_1$-$C_{12})$-alkyl]$_2$, —CO—$(C_1$-$C_{12})$-alkyl, —CO—$(C_6$-$C_{20})$-aryl, —COOH, —OH, —$SO_3H$, —$SO_3Na$, —$NO_2$, —CN, —$NH_2$, —N[$(C_1$-$C_{12})$-alkyl]$_2$.

In one embodiment, $R^9$, $R^{10}$, $R^{11}$, $R^{12}$, $R^{13}$, $R^{14}$, $R^{15}$, $R^{16}$ are each independently selected from:

—H, —$(C_1$-$C_{12})$-alkyl, —O—$(C_1$-$C_{12})$-alkyl, —O—$(C_6$-$C_{20})$-aryl, —$(C_6$-$C_{20})$-aryl, —COO—$(C_1$-$C_{12})$-alkyl, —CONH—$(C_1$-$C_{12})$-alkyl, —$(C_6$-$C_{20})$-aryl-CON[$(C_1$-$C_{12})$-alkyl]$_2$, —CO—$(C_1$-$C_{12})$-alkyl, —CO—$(C_6$-$C_{20})$-aryl, —COOH, —OH, —$NH_2$, —N[$(C_1$-$C_{12})$-alkyl]$_2$.

In one embodiment, $R^9$, $R^{10}$, $R^{11}$, $R^{12}$, $R^{13}$, $R^{14}$, $R^{15}$, $R^{16}$ are each independently selected from:

—H, —$(C_1$-$C_{12})$-alkyl, —O—$(C_1$-$C_{12})$-alkyl, —O—$(C_6$-$C_{20})$-aryl, —$(C_6$-$C_{20})$-aryl, —COO—$(C_1$-$C_{12})$-alkyl, —N[$(C_1$-$C_{12})$-alkyl]$_2$.

In one embodiment, $R^9$, $R^{10}$, $R^{11}$, $R^{12}$, $R^{13}$, $R^{14}$, $R^{15}$, $R^{16}$ are each independently selected from:

—H, —$(C_1$-$C_{12})$-alkyl, —O—$(C_1$-$C_{12})$-alkyl, —$(C_6$-$C_{20})$-aryl, where alkyl comprises 1-12 carbon atoms, preferably 1-10 carbon atoms, for example primary, secondary or tertiary alkyl groups such as methyl, ethyl, n-propyl, isopropyl, butyl, sec-butyl, t-butyl, t-butylethyl, t-butylpropyl, n-hexyl, amyl, sec-amyl, t-amyl, isooctyl, 2-ethylhexyl, decyl, dodecyl and octadecyl groups.

In one embodiment, $R^{11}$ and $R^{14}$ are each —O—$(C_1$-$C_{12})$-alkyl.

In one embodiment, $R^{11}$ and $R^{14}$ are each —OMe.

In one embodiment, $R^9$ and $R^{16}$ are each —$(C_1$-$C_{12})$-alkyl.

In one embodiment, $R^9$ and $R^{16}$ are each tert-butyl.

In one embodiment, $R^9$, $R^{11}$, $R^{14}$ and $R^{16}$ are each —$(C_1$-$C_{12})$-alkyl.

In one embodiment, $R^9$, $R^{11}$, $R^{14}$ and $R^{16}$ are each methyl.

In one embodiment, $R^9$, $R^{11}$, $R^{14}$ and $R^{16}$ are each tert-butyl.

In one embodiment, $R^9$, $R^{10}$, $R^{11}$, $R^{12}$, $R^{13}$, $R^{14}$, $R^{15}$ and $R^{16}$ are each —H.

In preferred embodiments, monophosphite compounds of the invention have one of the eight following general structures IV, V, VI, VII, VIII, IX, X and XI:

IV

V
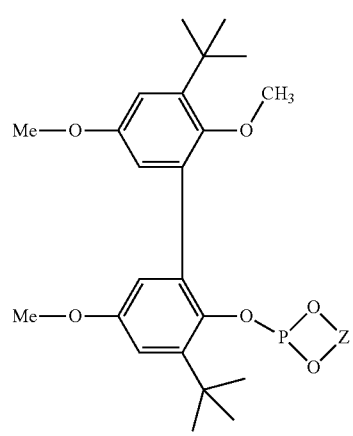
VI
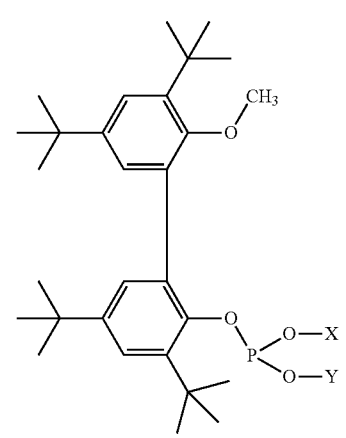
VII
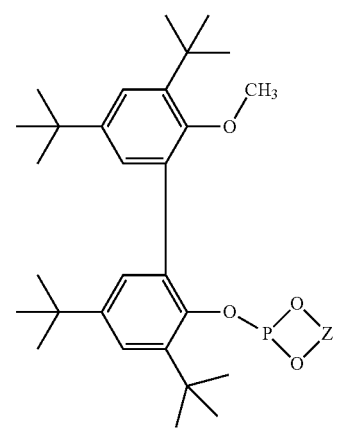
VIII
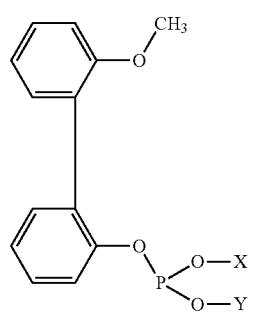
IX
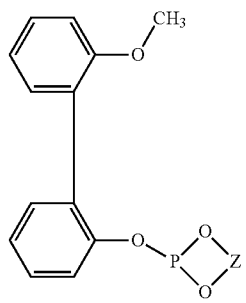
X
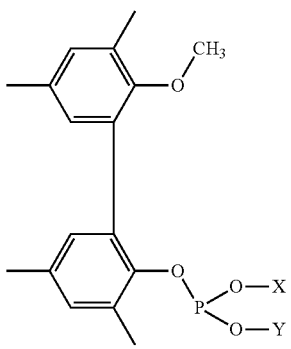
XI
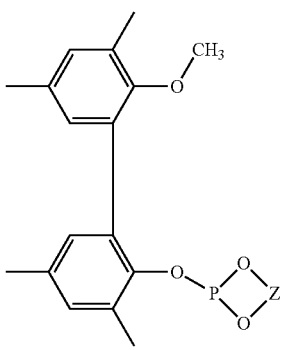
Particularly preferred compounds of the invention have, for example, one of the following structures L1, L2 or L3:
L1
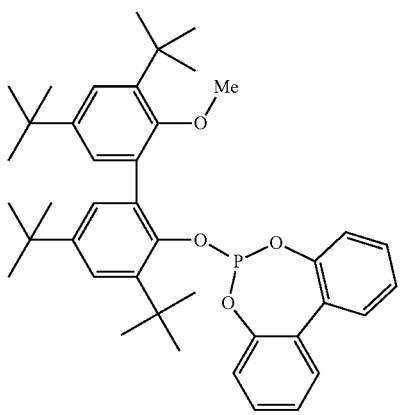

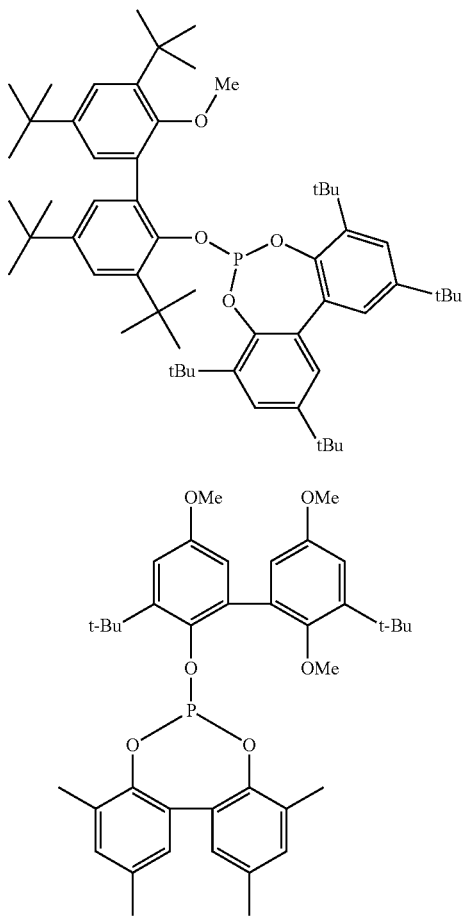

The monophosphite compounds of the invention are notable particularly for good stability and hence good storage stability; more particularly, the monophosphite compounds of the invention are more stable and easier to synthesize than the phosphonites known from DE 199 54 721 A1.

The invention additionally also relates to a process for preparing compounds having one of the two general structures I and II:

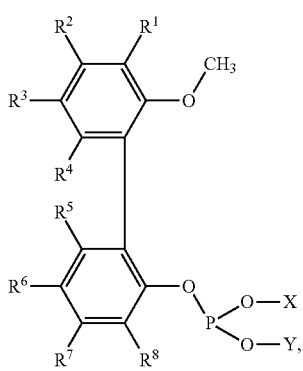

I

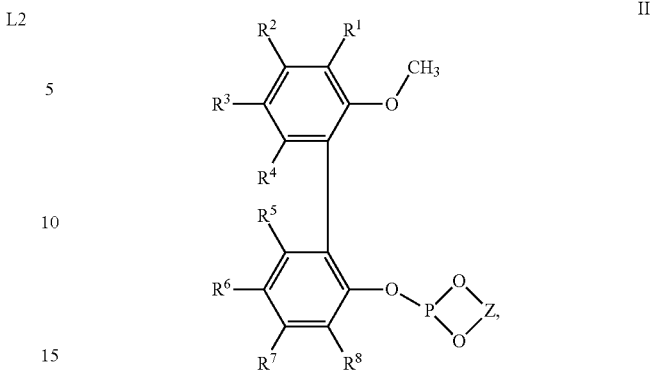

II where $R^1$, $R^2$, $R^3$, $R^4$, $R^5$, $R^6$, $R^7$, $R^8$ are each independently selected from:

—H, —$(C_1$-$C_{12})$-alkyl, —O—$(C_1$-$C_{12})$-alkyl, —O—$(C_6$-$C_{20})$-aryl, —$(C_6$-$C_{20})$-aryl, —Cl, —F, —Br, —I, —COO—$(C_1$-$C_{12})$-alkyl, —CONH—$(C_1$-$C_{12})$-alkyl, —$(C_6$-$C_{20})$-aryl-CON[$(C_1$-$C_{12})$-alkyl]$_2$, —CO—$(C_1$-$C_{12})$-alkyl, —CO—$(C_6$-$C_{20})$-aryl, —COOH, —OH, —SO$_3$H, —SO$_3$Na, —NO$_2$, —CN, —NH$_2$, —N[$(C_1$-$C_{12})$-alkyl]$_2$;

where X and Y are each independently selected from:

—$(C_1$-$C_{12})$-alkyl, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_1$-$C_{12})$-alkyl-$(C_6$-$C_{20})$-aryl, —$(C_6$-$C_{20})$-aryl-COO—$(C_1$-$C_{12})$-alkyl, —$(C_6$-$C_{20})$-aryl-CONH—$(C_1$-$C_{12})$-alkyl, —$(C_6$-$C_{20})$-aryl-CON[$(C_1$-$C_{12})$-alkyl]$_2$, —$(C_4$-$C_{20})$-heteroaryl, —$(C_4$-$C_{20})$-heteroaryl-$(C_1$-$C_{12})$-alkyl, —$(C_5$-$C_8)$-cycloalkyl, —$(C_6$-$C_{20})$-aryl-CO—$(C_6$-$C_{20})$-aryl;

and where Z is selected from:

—$(C_1$-$C_{12})$-alkyl, —$(C_6$-$C_{20})$-aryl, —$(C_6$-$C_{20})$-aryl-$(C_1$-$C_{12})$-alkyl, —$(C_1$-$C_{12})$-alkyl-O—$(C_6$-$C_{20})$-aryl, —$(C_4$-$C_{20})$-heteroaryl-, —$(C_6$-$C_{20})$-aryl-CO—$(C_6$-$C_{20})$-aryl-, —$(C_6$-$C_{20})$-aryl-$(C_6$-$C_{20})$-aryl-;

and where the alkyl, heteroalkyl, cycloalkyl, heterocycloalkyl, aryl and heteroaryl groups are optionally substituted, especially each independently by —$(C_1$-$C_{12})$-alkyl, —O—$(C_1$-$C_{12})$-alkyl, —O—$(C_6$-$C_{20})$-aryl, —$(C_6$-$C_{20})$-aryl, —Cl, —F, —Br, —I, COO—$(C_1$-$C_{12})$-alkyl, CONH—$(C_1$-$C_{12})$-alkyl, —$(C_6$-$C_{20})$-aryl-CON[$(C_1$-$C_{12})$-alkyl]$_2$, —CO—$(C_1$-$C_{12})$-alkyl, —CO—$(C_6$-$C_{20})$-aryl, —COOH, —OH, —SO$_3$H, —SO$_3$Na, —NO$_2$, —CN, —NH$_2$, —N[$(C_1$-$C_{12})$-alkyl]$_2$.

The process of the invention for preparing monophosphite compounds has the following steps a)-d), the sequence of which need not necessarily correspond to the sequence in which they are named:

a) initially charging a reactant,
b) adding a methylating reagent,
c) adding a compound containing or consisting of phosphorus and chlorine, and
d) obtaining a product.

By way of example, three embodiments of the preparation process of the invention are described in simplified form hereinafter. It is pointed out that the bases and methylating reagents mentioned by way of example in the description of the individual embodiments of the process may be replaced by other bases and methylating reagents known to those skilled in the art, and that base can additionally be used if required in any step.

The first embodiment of the process of the invention for preparing compounds having a structure of formula I or II comprises essentially three synthesis stages shown in reaction schemes 1a and 1b. Reaction scheme 1a shows the preparation of monophosphite compounds having a structure of formula I:

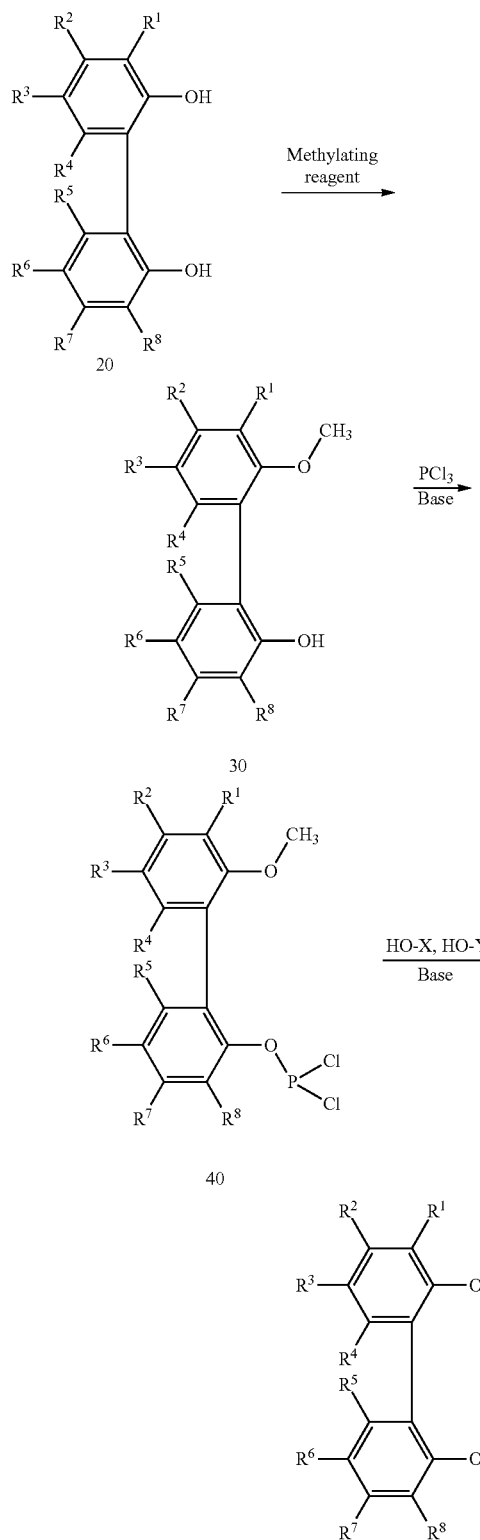

Reaction scheme 1a: Preparation of monophosphite compounds of the invention having a structure of formula I in a first embodiment of the process In the first stage of the synthesis of compounds having a structure of formula I shown in reaction scheme 1a, methylation of the hydroxyl group present in the para position to the $R^3$ substituent of a biphenol derivative 20 is effected by reaction with a methylating reagent, for example with dimethyl sulphate or MeI, which affords the compound 30. In the second synthesis stage, $PCl_3$ is added to the methylated compound 30, which reacts in the presence of a base, for example triethylamine, with the non-methylated hydroxyl group (in the para position to the $R^6$ substituent) with elimination of HCl or with formation of the corresponding amine hydrochloride, which is formed by reaction of the base with the HCl released, to give the chlorophosphite 40. In the third synthesis stage, reaction with the alcohols HO—X and HO—Y, likewise with elimination of HCl or with formation of the amine hydrochloride formed by reaction of the base, for example triethylamine, with the HCl released, results in the conversion to the monophosphite compound of formula I.

Reaction scheme 1b shows the preparation of monophosphite compounds having a structure of formula II:

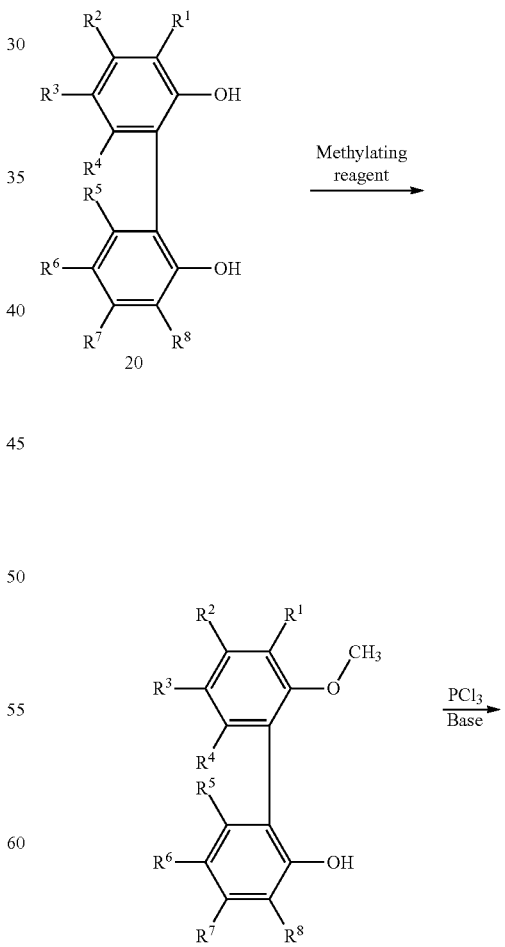

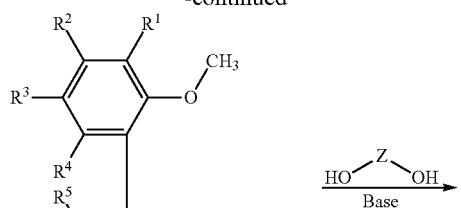

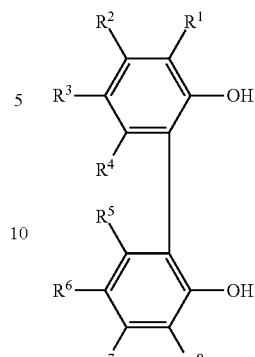

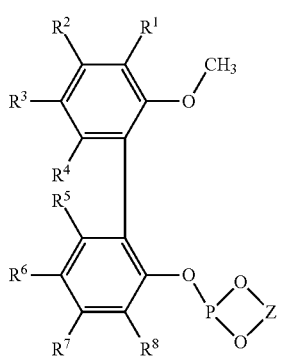

II

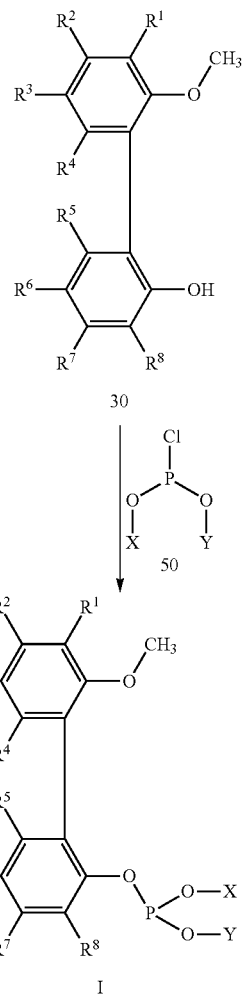

Reaction scheme 1b: Preparation of monophosphite compounds of the invention having a structure of formula II in a first embodiment of the process The synthesis of compounds having a structure of formula II shown in reaction scheme 1b, up to the preparation of the chlorophosphite 40, proceeds in an identical manner to the synthesis of compounds having a structure of formula I shown in reaction scheme 1a. However, the chlorophosphite 40, in a departure from the synthesis shown in reaction scheme 1 a, is not reacted with the alcohols HO—X and HO—Y, but with a diol having the Z group to give the monophosphite compound having a structure of formula II.

In summary, the process of the invention thus features, in the first embodiment, the presence of the chlorophosphite 40 as an intermediate.

The second embodiment of the process of the invention for preparing compounds having a structure of formula I or II comprises essentially two synthesis stages. Reaction scheme 2a shows the preparation of monophosphite compounds having a structure of formula I, while reaction scheme 2b shows the preparation of monophosphite compounds having a structure of formula II.

Reaction scheme 2a: Preparation of monophosphite compounds of the invention having a structure of formula I in a second embodiment of the process In the embodiment of the process of the invention shown in reaction scheme 2a, in the first synthesis stage, a hydroxyl group of a biphenol derivative 20 is first methylated by reaction with a methylating reagent, for example dimethyl sulphate or MeI. This synthesis step corresponds to that in the first synthesis stage in the first embodiment of the process of the invention shown in reaction schemes 1a and 1b. The methylated reaction product 30 of the first synthesis stage is then, in contrast with the first embodiment of the process of the invention, not converted to a chlorophosphite but reacted with a chlorophosphite, namely the chlorophosphite of the general structure 50. Synthesis routes for preparation of chlorophosphites are sufficiently well known to those skilled in the art; in addition, the synthesis of selected chlorophosphites will be described later on. The reaction product formed in the second synthesis stage is a monophosphite compound of the invention having a structure of formula I.

Monophosphite compounds of the invention having a structure of formula II are, in the second embodiment of the process of the invention, obtainable in accordance with the synthesis route shown in reaction scheme 2b.

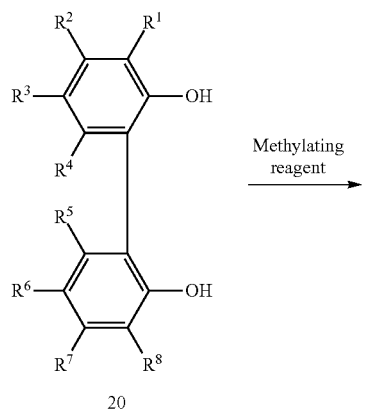

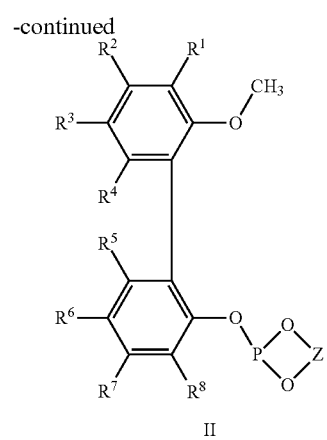

II

Reaction scheme 2b: Preparation of monophosphite compounds of the invention having a structure of formula II in a second embodiment of the process The first synthesis stage of the process shown in reaction scheme 2b is the methylation of the compound 20 to give the intermediate 30 already known from reaction scheme 2a. In the second synthesis stage, as in the reaction route shown in reaction scheme 2a as well, the compound 30 is reacted with a chlorophosphite. However, the latter has a different structure from the chlorophosphite used in the reaction in reaction scheme 2a, namely the structure of the general formula 60, such that the reaction product formed is the monophosphite compound having a structure of formula II. As already mentioned in connection with the synthesis route shown in reaction scheme 2a, routes for preparation of chlorophosphites are sufficiently well known to those skilled in the art. The preparation of selected chlorophosphites is additionally described later on.

In summary, it is a feature of the process of the invention in the second embodiment that it includes the reaction of a biphenol derivative 20 with a chlorophosphite of the general structure 50 or 60.

In a third embodiment of the process of the invention for preparing compounds having a structure of formula I or II, the methylation which formed the first synthesis stage in each of the first two embodiments is not effected until the last synthesis stage.

Reaction scheme 3a shows the preparation of monophosphite compounds having a structure of formula I in the third embodiment of the process:

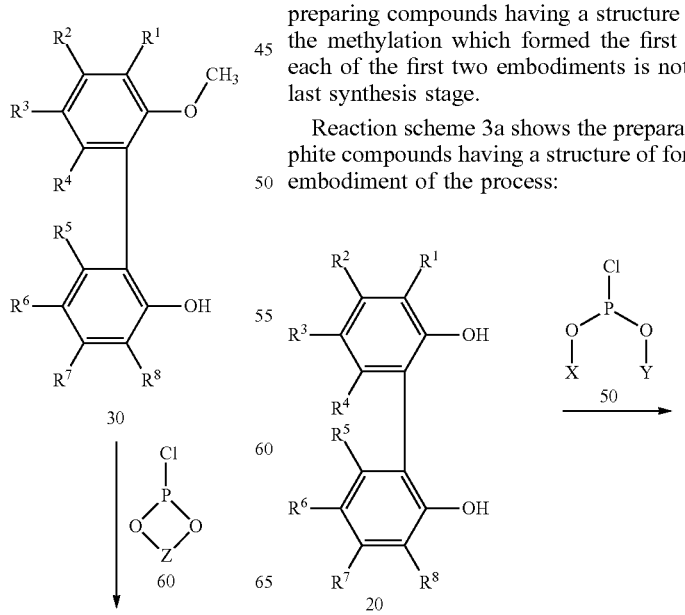

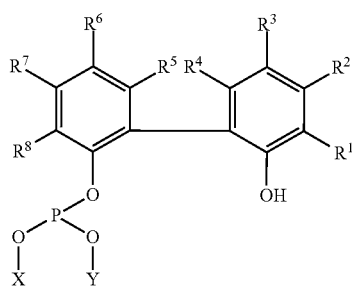

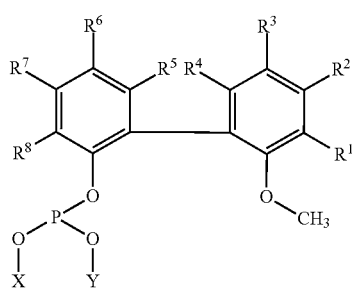

I

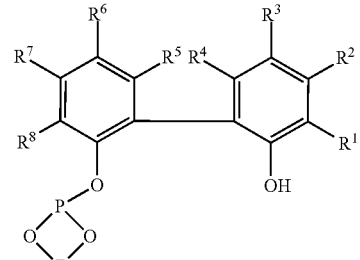

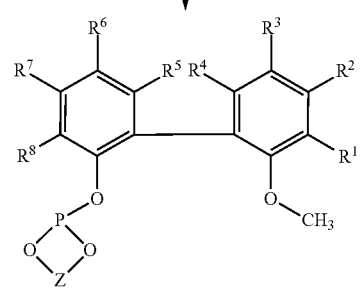

II

Reaction scheme 3a: Preparation of monophosphite compounds of the invention having a structure of formula I in a third embodiment of the process In the first stage of the synthesis of compounds having a structure of formula I shown in reaction scheme 3a, a biphenol derivative 20 is reacted with a chlorophosphite 50 to give a monophosphite compound which differs from a monophosphite compound of the invention having a structure of formula I merely in that it has a hydroxyl group rather than a methyl group bonded via an oxygen atom in the para position to the $R^3$ substituent. In the second synthesis stage, the methylation is then effected in the para position to the $R^3$ substituent, for example by reaction with dimethyl sulphate or MeI, which affords a compound having a structure of formula I.

For monophosphite compounds of formula II, the synthesis route according to the third embodiment is shown in reaction scheme 3b:

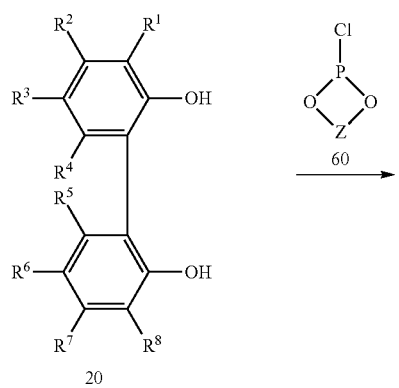

Reaction scheme 3b: Preparation of monophosphite compounds of the invention having a structure of formula II in a third embodiment of the process In the first stage of the synthesis of compounds having a structure of formula II shown in reaction scheme 3b, a biphenol derivative 20 is reacted with a chlorophosphite 60 to give a monophosphite compound which differs from a monophosphite compound of the invention having a structure of formula II merely in that it has a hydroxyl group rather than a methyl group bonded via an oxygen atom in the para position to the $R^3$ substituent. In the second synthesis stage, the methylation is then effected in the para position to the $R^3$ substituent, for example by reaction with dimethyl sulphate or MeI, which affords a compound having a structure of formula II.

The substituents $R^1$, $R^2$, $R^3$, $R^4$, $R^5$, $R^6$, $R^7$, $R^8$, X, Y and Z are not newly defined in every general structure shown in the present application. However, it is intended that the substituents $R^1$, $R^2$, $R^3$, $R^4$, $R^5$, $R^6$, $R^7$, $R^8$, X, Y and Z in every general structure in which they are present are defined in an identical manner to the definition given in connection with the formulae I and II.

The invention also relates to the use of a compound having a structure of formula I or II as ligand in a ligand-metal complex for catalysis of hydroformylation reactions, and to a hydroformylation process in which the compound is used as ligand in a ligand-metal complex for conversion of an olefin to an aldehyde.

Complexes of the invention include a metal atom or ion and at least one monophosphite compound having a structure of formula I or formula II as ligand. The metal atom or ion may especially be selected from the group comprising rhodium, cobalt, iridium and ruthenium. More preferably, the metal atom or ion is rhodium. Optionally, the complex of the invention may also have two or more monophosphite compounds having a structure of formula I and/or formula II as ligands, where the monophosphite compounds may have an identical or different structure.

In this regard, see R. Franke, D. Selent, A. Börner, "Applied Hydroformylation", Chem. Rev., 2012, DOI: 10.1021/cr3001803; p. 5688, Scheme 12 "General Method for the Preparation of a P-Modified Rh precatalyst" and references cited therein, and also P. W. N. M. van Leeuwen, in Rhodium Catalyzed Hydroformylation, P. W. N. M. van Leeuwen, C. Claver (eds.), Kluwer, Dordrecht, 2000, inter alia p. 48 ff., p. 233 ff. and references cited therein, and also K. D. Wiese and D. Obst in Top. Organomet. Chem. 2006, 18, 1-13; Springer Verlag Berlin Heidelberg 2006 p. 6 ff. and references cited therein.

A particular advantage of monophosphite compounds of the invention and complexes of the invention in hydroformylation is that they can also be used as ligands or catalysts in the conversion of technical olefin mixtures to aldehydes. Preferably, monophosphite compounds of the invention and complexes including them additionally feature a good to very good yield when used in hydroformylation reactions.

The hydroformylation process in which monophosphite compounds of the invention are used as ligand for conversion of an olefin to an aldehyde comprises the following process steps:
a) initially charging an olefin,
b) adding a complex of the invention or alternatively a compound of the invention and a compound containing a metal atom or metal ion, the metal atom or metal ion preferably being selected from Rh, Ru, Co and Ir,
c) feeding in $H_2$ and CO,
d) heating the reaction mixture, with conversion of the olefin to an aldehyde.

Process steps a) to d) can be effected here in any desired sequence.

The reaction is typically conducted under customary conditions that are sufficiently well known to those skilled in the art.

Preference is given to a temperature of 80° C. to 160° C. and a pressure of 1 to 300 bar.

Particular preference is given to a temperature of 100° C. to 160° C. and a pressure of 15 to 250 bar.

In a preferred embodiment, the metal is Rh.

The process of the invention using the compounds of the invention can be used to hydroformylate α-olefins, terminally branched, internal and internally branched olefins.

The reactants for the hydroformylation in the process of the invention are olefins or mixtures of olefins, especially monoolefins having 2 to 24, preferably 3 to 16 and more preferably 3 to 12 carbon atoms, having terminal or internal C—C double bonds, for example 1-propene, 1-butene, 2-butene, 1- or 2-pentene, 2-methyl-1-butene, 2-methyl-2-butene, 3-methyl-1-butene, 1-, 2- or 3-hexene, the $C_6$ olefin mixture obtained in the dimerization of propene (dipropene), heptenes, 2- or 3-methyl-1-hexenes, octenes, 2-methylheptenes, 3-methylheptenes, 5-methyl-2-heptene, 6-methyl-2-heptene, 2-ethyl-1-hexene, the $C_8$ olefin mixture obtained in the dimerization of butenes (di-n-butene, diisobutene), nonenes, 2- or 3-methyloctenes, the $C_9$ olefin mixture obtained in the trimerization of propene (tripropene), decenes, 2-ethyl-1-octene, dodecenes, the $C_{12}$ olefin mixture obtained in the tetramerization of propene or the trimerization of butenes (tetrapropene or tributene), tetradecenes, hexadecenes, the $C_{16}$ olefin mixture obtained in the tetramerization of butenes (tetrabutene), and olefin mixtures prepared by cooligomerization of olefins having different numbers of carbon atoms (preferably 2 to 4).

The invention is now described in detail with reference to working examples, which especially includes the preparation of monophosphite compounds of the invention or intermediates thereof.

General Procedures:

All the preparations described hereinafter were conducted under protective gas using standard Schlenk techniques. The solvents were dried over suitable desiccants before use (Purification of Laboratory Chemicals, W. L. F. Armarego, Christina Chai, Butterworth Heinemann (Elsevier), 6th edition, Oxford 2009). All preparative operations were effected in baked-out vessels.

The products were characterized by means of NMR spectroscopy. Chemical shifts (δ) are reported in ppm. The 31P NMR signals were referenced according to: SR31P=SR1H*(BF31P/BF1 H)=SR1H*0.4048. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84).

Nuclear resonance spectra were recorded by means of a Bruker Avance 300 or Bruker Avance 400; gas chromatography analysis was effected using an Agilent GC 7890A.

Introduction of the Me Group

Example 1

Preparation of 3,3'-di-tert-butyl-2',5,5'-trimethoxy-[1,1'-biphenyl]-2-ol

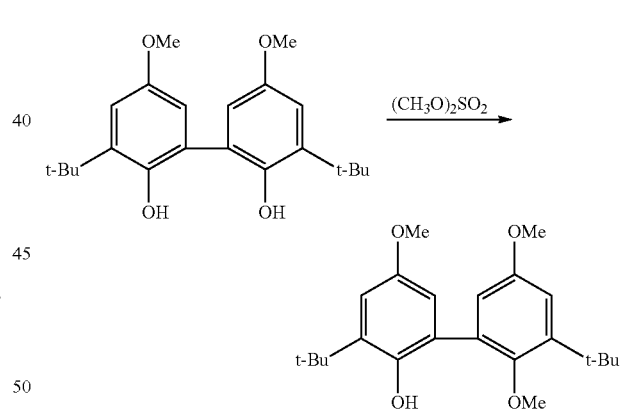

In a 1 l Schlenk flask which had been repeatedly evacuated and filled with inert gas, 37.6 g (0.104 mol) of 3,3'-di-tert-butyl-5,5'-dimethoxy[1,1'-biphenyl]-2,2'-diol and 17.3 g (0.124 mol) of potassium carbonate (anhydrous) were initially introduced and were dissolved with stirring in 10.0 ml (0.104 mol) of dimethyl sulphate and 380 ml of dried acetone. The resulting suspension was boiled under reflux for 7.5 hours and then cooled to room temperature.

Subsequently 100 ml of a 2-molar ammonia solution were added, followed by stirring at room temperature for 4 hours. This was followed by extraction by shaking with 200 ml of methylene chloride, and the aqueous alkaline phase was acidified using 1-molar hydrochloric acid solution (about 280 ml), and was then again extracted by shaking with 3 times 100 ml of methylene chloride. The organic phases obtained were combined and extracted by shaking with 1-molar hydrochloric acid solution (100 ml).

The organic phase was washed a further 3 times with DI water (200 ml) and dried over magnesium sulphate. The solvent was removed under reduced pressure and the oil obtained was washed with 50 ml of isopropanol, filtered and then dried. The product was obtained as a white solid in 30.8 g (74.9% yield).

Example 2

Preparation of 3,3',5,5'-tetra-tert-butyl-2-methoxy-[1,1'-biphenyl]-2-ol

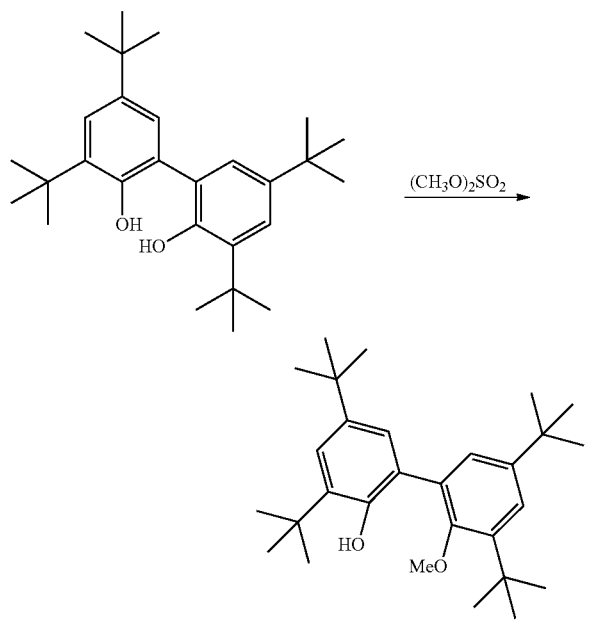

In a 1000 ml Schlenk flask which had been repeatedly evacuated and filled with inert gas, 43 g (0.104 mol) of 3,3',5,5'-tetra-tert-butyl-[1,1'-biphenyl]-2,2'-diol and 21.6 g (0.154 mol) of potassium carbonate were initially introduced and were dissolved with stirring in 10.00 ml (0.104 mol) of dimethyl sulphate and 430 ml of dried acetone. The resulting suspension was boiled under reflux for 6 hours and then cooled to room temperature.

Following addition of 110 ml of 2-molar ammonia solution, stirring took place for 4 hours. This was followed by extraction by shaking with 200 ml of methylene chloride, and the aqueous alkaline phase was acidified using 1-molar hydrochloric acid solution (about 280 ml), and was then again extracted by shaking with 3 times 100 ml of methylene chloride. The organic phases obtained were combined and extracted by shaking with 1-molar hydrochloric acid solution (100 ml).

The organic phase was washed a further 3 times with DI water (200 ml) and dried over magnesium sulphate. The solvent was removed under reduced pressure and the oil obtained was washed with 50 ml of isopropanol, filtered and then dried. The product was obtained as a white solid in 33.5 g (75% yield).

Synthesis of the Chlorophosphites:

6-Chlorodibenzo[d,f][1,3,2]dioxaphosphepin was prepared according to DE 10 2008 043 584, and 2-chloro-4,4,5,5-tetraphenyl-1,3,2-dioxaphospholane according to DE 10 2006 058 682.

The preparation of 2,2'-bis(3,5-di-tert-butyl)phenol chlorophosphite was effected according to the following protocol:

Example 3

Preparation of 2,2'-bis(3,5-di-tert-butyl)phenol chlorophosphite

In a 500 ml Schlenk flask which had been repeatedly evacuated and filled with inert gas, 41 g (0.1 mol) of 2,2'-bis(3,5-di-tert-butyl)phenol and 30.7 g (42.3 ml; 0.3 mol) of dried triethylamine were dissolved in 300 ml of dried toluene.

In a second Schlenk flask (1000 ml) which had been repeatedly evacuated and filled with inert gas, 13.9 g (8.8 ml; 0.1 mol) of phosphorus trichloride were dissolved in 600 ml of dried toluene, and the diphenol-triethylamine-toluene solution prepared beforehand was added dropwise to this solution with vigorous stirring, slowly and steadily, at a temperature between −5 and 0° C. The solution was allowed to warm to room temperature overnight. The ammonium chloride formed was removed by filtration, and the solvent was concentrated to dryness under reduced pressure. The product was obtained in 98% yield (47 g).

All other chlorophosphites can be prepared analogously, i.e. by addition of phosphorus trichloride in the presence of a base. In this regard, see also "Phosphorus(III) Ligands in Homogeneous Catalysis—Design and Synthesis" by Paul C. J. Kamer and Piet W. N. M. van Leeuwen; John Wiley and Sons, 2012; including p. 94 ff. and references cited therein.

Example 4

Preparation of biphenyl-3,3',5,5'-tetra-tert-butyl-2-hydroxy-2'-dichlorophosphite

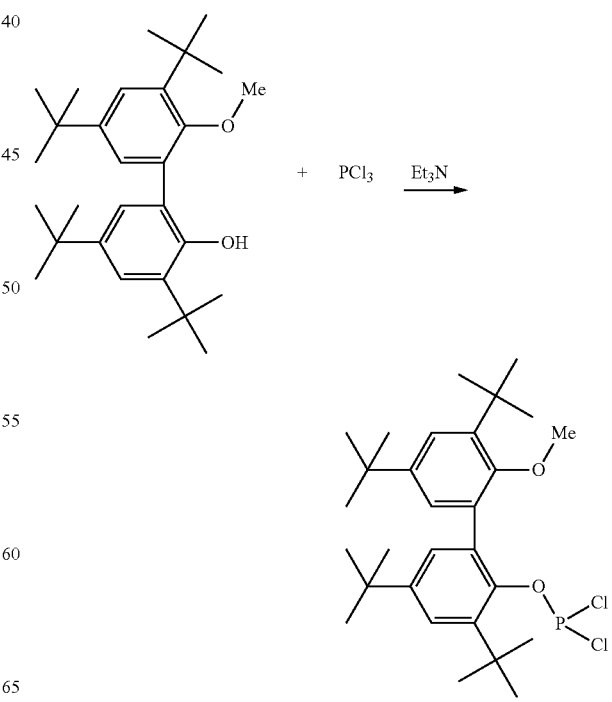

In a 250 ml Schlenk flask which had been repeatedly evacuated and filled with inert gas, 10.62 g (0.025 mol) of 3,3',5,5'-tetra-tert-butyl-2-hydroxy-2'-methoxybiphenyl were dissolved with stirring in 50 ml of dried toluene and admixed with 3.5 ml (0.025 mol) of triethylamine. Added dropwise to the resulting solution, at room temperature and with vigorous stirring, are 2.2 ml (0.025 mol) of phosphorus trichloride, and the mixture is then heated at 105° C. for 4 hours. It is worked up by filtering off the precipitated ammonium chloride and washing the filter product 2 times with 25 ml of toluene. The filtrate is concentrated to dryness. The product was obtained in 63% yield.

Example 5

Preparation of dichloro((3,3'-di-tert-butyl-2',5,5'-trimethoxy-[1,1'-biphenyl]-2-yl)oxy)phosphine

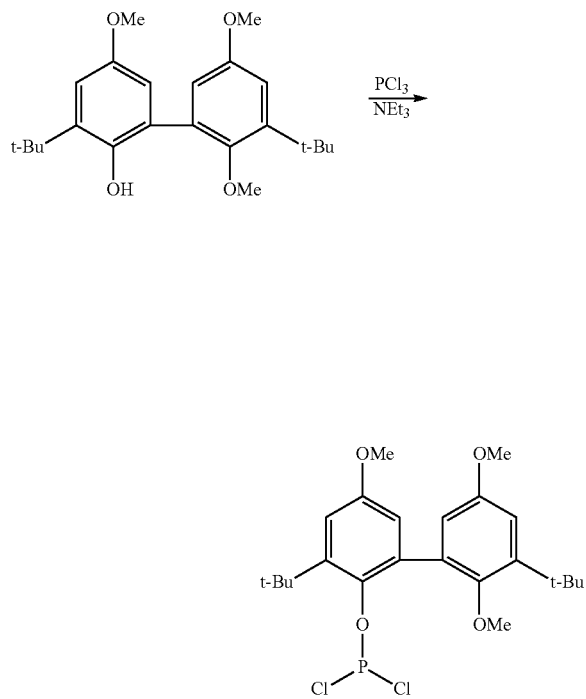

In a 250 ml Schlenk flask which had been repeatedly evacuated and filled with inert gas, 28.4 g (0.072 mol) of 3,3'-di-tert-butyl-2',5,5'-trimethoxy[1,1'-biphenyl]-2-ol were dissolved with stirring in 200 ml of dried toluene and 40.0 ml (0.282 mol) of degassed triethylamine.

A second 500 ml Schlenk flask is initially charged with 200 ml of dried toluene and then 25 ml (0.281 mol) of phosphorus trichloride are added. Then, with vigorous stirring, the phenol/amine/toluene solution prepared beforehand is added dropwise at room temperature over the course of 1 hour to the phosphorus trichloride/toluene solution. Following complete addition, heating takes place at 80° C. for 4 hours, followed by cooling to room temperature overnight.

The reaction mixture is filtered, washed with three times 50 ml of dried toluene, and the filtrate is concentrated to dryness. The product was obtained in 83% yield (35.3 g).

Synthesis of the Monophosphites

Example 6

Preparation of 6-((3,3',5,5'-tetra-tert-butyl-2'-methoxy-[1,1'-biphenyl]-2-yl)oxy)dibenzo[d,f][1,3,2]dioxaphosphepin

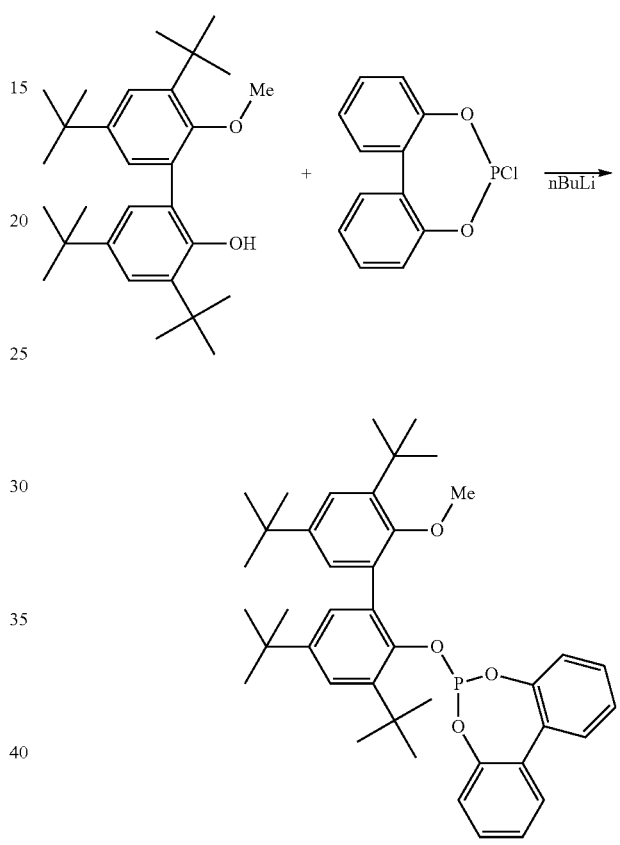

In a 250 ml Schlenk flask which had been repeatedly evacuated and filled with inert gas, 5 g (0.012 mol) of 3,3',5,5'-tetra-tert-butyl-2-hydroxy-2'-methoxybiphenyl were dissolved in 50 ml of dried THF. Then 7.5 ml of butyllithium (1.6-molar solution, 0.012 mol) were added dropwise with vigorous stirring at −20° C. to the tetrahydrofuran/phenol mixture. Following complete addition, the mixture was stirred at 0° C. for an hour. In a second Schlenk flask (100 ml) which had been repeatedly evacuated and filled with inert gas, 3 g (0.012 mol) of 6-chlorodibenzo[d,f][1,3,2]dioxaphosphepin were dissolved with stirring in 50 ml of dried THF. The chlorophosphite solution was then added dropwise to the pre-prepared phenol solution at 0° C. with vigorous stirring. The reaction mixture was heated at 60° C. for 2 hours. After the mixture had cooled to room temperature, the solvent was removed under reduced pressure.

The residue obtained was taken up in 50 ml of methylene chloride, filtered to remove the lithium chloride, then concentrated to dryness again and washed with isopropanol. The product was obtained in 5.5 g (72.8%).

Example 7

Preparation of 2,4,8,10-tetra-tert-butyl-6-((3,3',5,5'-tetra-tert-butyl-2'-methoxy-[1,1'-biphenyl]-2-yl)oxy)dibenzo[d,f][1,3,2]dioxaphosphepin

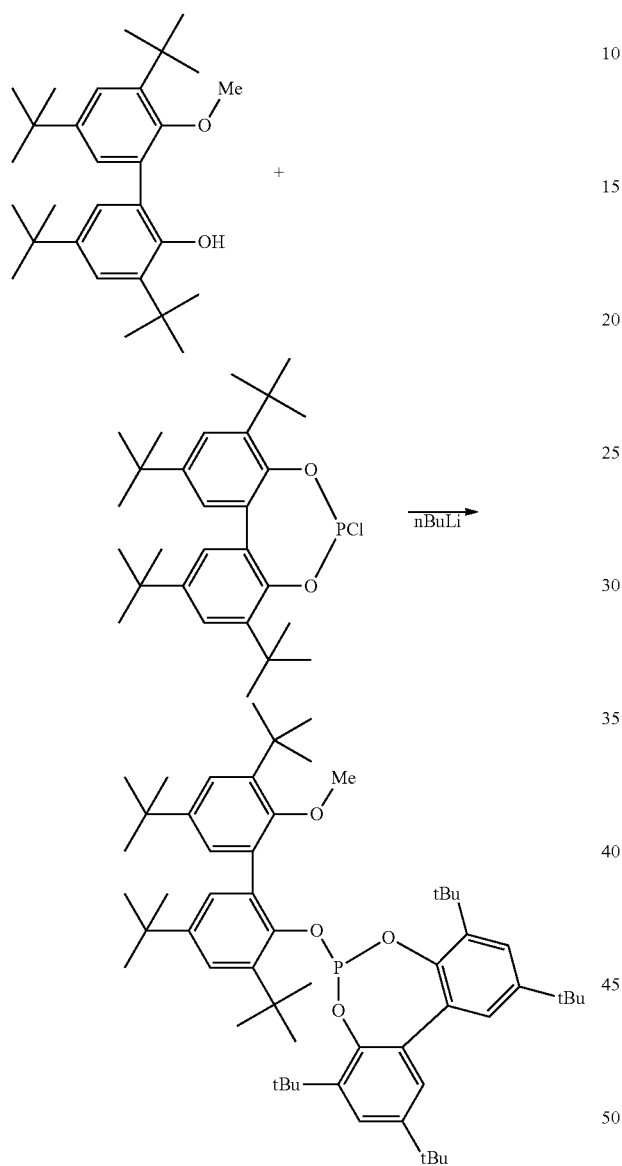

In a 250 ml Schlenk flask which had been repeatedly evacuated and filled with inert gas, 5 g (0.012 mol) of 3,3',5,5'-tetra-tert-butyl-2-hydroxy-2'-methoxybiphenyl were dissolved in 50 ml of dried THF and admixed at −20° C. with 7.5 ml of butyllithium (1.6-molar solution, 0.012 mol). Following complete addition, stirring took place at 0° C. for a further hour. In a second Schlenk flask (100 ml) which had been repeatedly evacuated and filled with inert gas, 5.7 g (0.012 mol) of 2,2'-bis(3,5-di-tert-butyl)phenol chlorophosphite were dissolved with stirring in 50 ml of dried THF. The chlorophosphite solution was then added dropwise with vigorous stirring to the pre-prepared phenol solution at 0° C. Following complete addition, the reaction mixture was warmed slowly to room temperature overnight. The reaction mixture was then heated at 60° C. for 20 hours. For working up, the solvent was removed under reduced pressure at room temperature. The residue obtained was taken up in 50 ml of methylene chloride, and the lithium chloride which remained was removed by filtration. The resulting filtrate was washed with about 40 ml of dried acetonitrile, followed by further filtration. The residue was washed with about 50 ml of isopropanol and about 50 ml of pentane. The product was obtained in 35% yield.

Example 8

Preparation of bis(2,4-di-tert-butylphenyl)-(3,3',5,5'-tetra-tert-butyl-2'-methoxy-[1,1'-biphenyl]-2-yl)phosphite

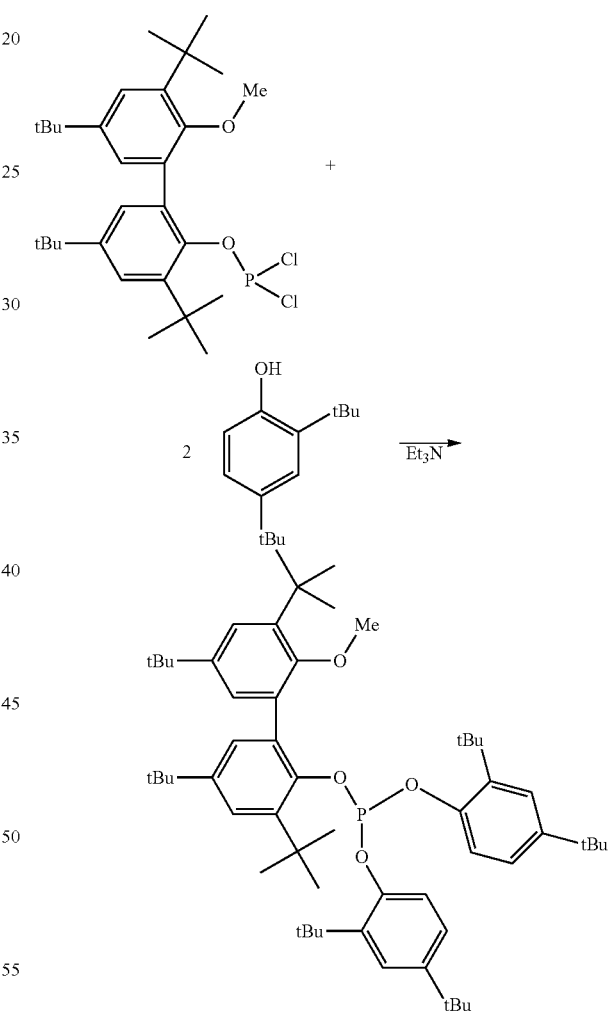

In a 250 ml Schlenk flask which had been repeatedly evacuated and filled with inert gas, 2.6 g (0.012 mol) of 2,4-di-tert-butylphenol were dissolved with stirring in 100 ml of dried toluene and admixed with 3.5 ml (0.025 mol) of dried triethylamine. In a second Schlenk flask (100 ml) which had been repeatedly evacuated and filled with inert gas, 3.3 g (0.006 mol) of biphenyl-3,3',5,5'-tetra-tert-butyl-2-methoxy-2'-dichlorophosphite were dissolved with stirring in 100 ml of dried toluene. The chlorophosphite/toluene solution was subsequently added dropwise with vigorous stirring at 0-(−4)° C. to the phenol/amine/toluene solution, and the solution was allowed to warm to room temperature overnight.

The ammonium chloride was allowed to settle and a sample was taken, for conversion testing, from the supernatant solution, for the GC/MS. Thereafter the ammonium chloride formed was removed by filtration and the solvent was concentrated to dryness under reduced pressure. The resulting oil was recrystallized from dried acetonitrile and dried. The product was obtained in 52% yield.

Example 9

Preparation of 6-((3,3'-di-tert-butyl-2',5,5'-trimethoxy-[1,1'-biphenyl]-2-yl)oxy)-2,4,8,10-tetramethyldibenzo[d,f][1,3,2]dioxaphosphepin

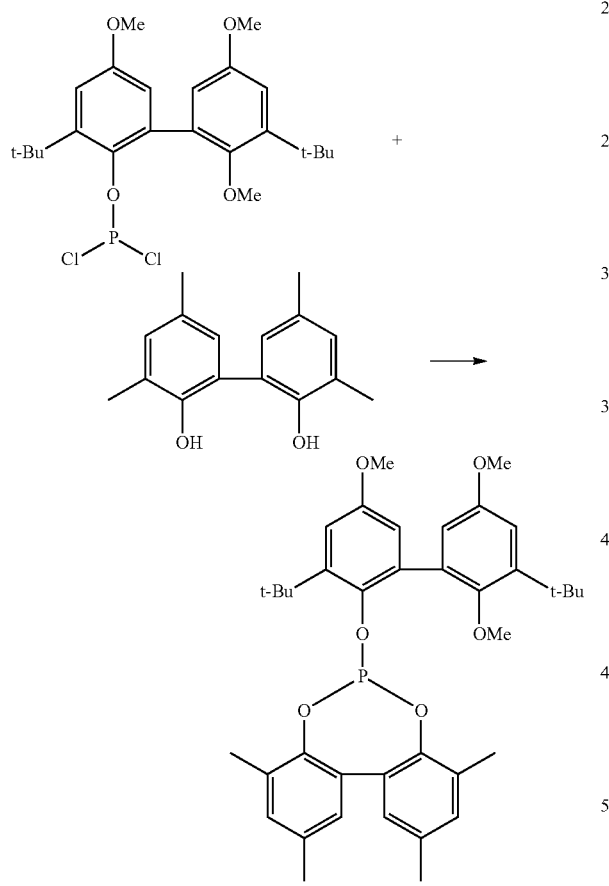

In a 500 ml Schlenk flask which had been repeatedly evacuated and filled with inert gas, 4.1 g (0.008 mol) of dichloro((3,3'-di-tert-butyl-2',5,5'-trimethoxy[1,1'-biphenyl]-2-yl)oxy)phosphine were dissolved in 100 ml of degassed acetonitrile. In a second Schlenk flask (500 ml) which had been repeatedly evacuated and filled with inert gas, 1.89 g (0.008 mol) of 3,3',5,5'-tetramethyl(1,1'-biphenyl)-2,2'-diol were dissolved in 100 ml of degassed acetonitrile and 2.3 ml (0.016 mol) of N,N'-dimethylaminobutane. The chlorophosphite solution was subsequently added dropwise, slowly and steadily, at room temperature to the "biphenol"-amine solution, and the combined solutions were stirred at room temperature for 2.5 hours.

The solvent was removed under reduced pressure at 40° C. and the residue obtained was taken up in toluene, the hydrochloride was removed by filtration, and the solvent was again removed under reduced pressure. The product was obtained in 72% yield (4.1 g).

Example 10

Preparation of 2,4,8,10-tetramethyl-6-((3,3',5,5'-tetra-tert-butyl-2'-methoxy-[1,1'-biphenyl]-2-yl)oxy)dibenzo[d,f][1,3,2]dioxaphosphepin

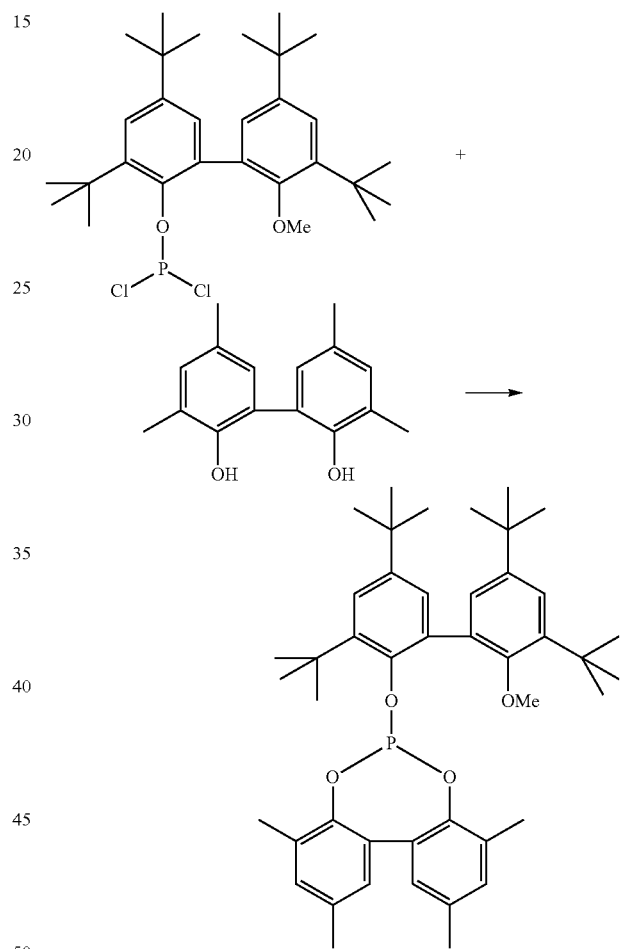

In a 250 ml Schlenk flask which had been repeatedly evacuated and filled with inert gas, 10 g (0.017 mol) of biphenyl 3,3',5,5'-tetra-tert-butyl-2-methoxy-2'-dichlorophosphite were dissolved in 50 ml of degassed toluene. In a second Schlenk flask (100 ml), 5 g (0.019 mol) of 3,3',5,5'-tetramethyl[1,1'-biphenyl]-2,2'-diol were dissolved in 50 ml of degassed toluene and 4 ml (0.029 mol) of degassed triethylamine. The phenol/amine/toluene solution was then added dropwise with vigorous stirring at room temperature to the chlorophosphite/toluene solution.

Following complete addition, the reaction mixture was heated at 80° C. for an hour and cooled back down to room temperature in an oil bath overnight.

For working up, the resulting amine hydrochloride was removed by filtration and the mother liquor obtained was concentrated to dryness under reduced pressure. The solids (8.7 g) were then dissolved once again in 30 ml of toluene. Another Schlenk vessel was charged with 260 ml of methanol, 13 ml of degassed water and 13 ml of degassed dimethylaminobutane. While stirring, the monophosphite/toluene solution was then added slowly at room temperature to the methanol solution, followed by stirring at room temperature for an hour, then by cooling to 0° C. with an ice bath, and then by stirring for two hours more. The resulting suspension was filtered. The product was obtained as a solid (6.4 g).

Procedure for the Catalysis Experiments:

In order to test the catalysis properties of the compounds or complexes of the invention, they were used in the hydroformylation of various olefins in accordance with the general experimental description which follows.

General Experimental Description:

In a 100 ml autoclave from Parr Instruments, various olefins were hydroformylated at various temperatures and at synthesis gas pressure 20 and 50 bar in each case (CO/$H_2$=1:1 (% by vol.)). As precursor, 0.005 g of Rh(acac)(CO)$_2$ was initially charged for a catalyst concentration of 40 ppm of Rh based on the overall reaction mixture, and correspondingly 0.0123 g of Rh(acac)(CO)$_2$ for a concentration of 100 ppm of Rh. The solvent used was 40 to 46 g of toluene in each case.

The compounds to be tested were used in different molar excesses relative to rhodium. In addition, as GC standard, about 0.5 g of tetraisopropylbenzene (TIPB) was added. About 6 g of reactant were metered in after the reaction temperature envisaged had been attained.

During the reaction, the pressure was kept constant via metered addition of synthesis gas with a mass flow meter and pressure regulator. The stirrer speed was 1200 min$^{-1}$. After 3 hours and after 12 hours, samples were taken from the reaction mixture.

Example 11

Catalysis Experiments with Compounds L1, L2 and L3

Compounds L1, L2 and L3, the structures of which are given below, were tested for their suitability for catalysis of hydroformylation reactions according to the general experimental description above.

L1

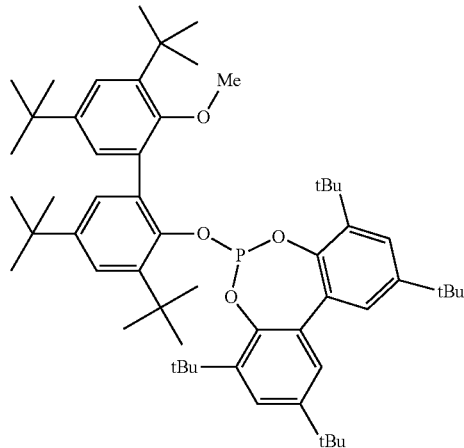

L2

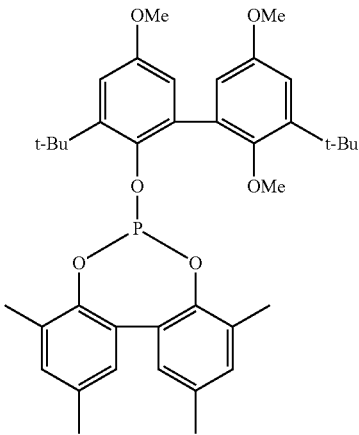

L3

Comparative compounds used were the noninventive compounds L4 and L5, the synthesis of which is elucidated hereinafter.

The compounds L4 and L5 are likewise monophosphite compounds, except that they bear a BOC group (tert-butyloxycarbonyl=BOC) rather than the Me group.

Synthesis Method for the Comparative Compounds:

Precursors:

Introduction of the BOC Group:

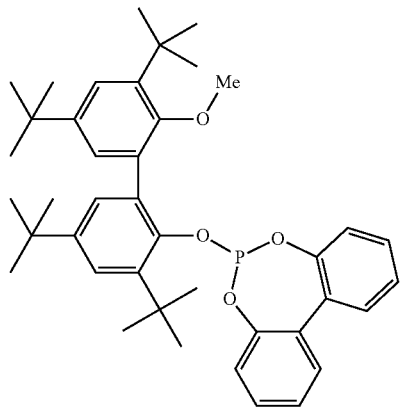 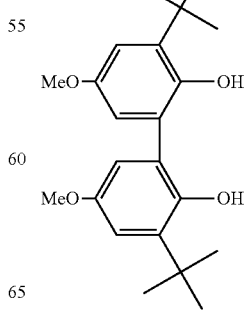 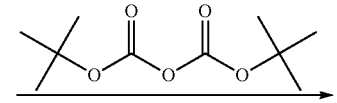

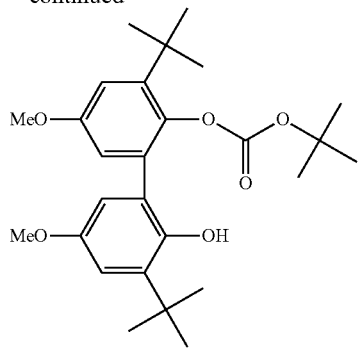

In a 2 l Schlenk flask, 400 mmol (143.8 g) of 3,3'-di-tert-butyl-5,5'-dimethoxy-[1,1'-biphenyl]-2,2'-diol and 40 mmol (4.8 g) of N,N-dimethylaminopyridine (DMAP) were dissolved in 900 ml of $CH_2Cl_2$. Subsequently, at room temperature, 400 mmol (88 g) of di-tert-butyl dicarbonate were dissolved in 280 ml of $CH_2Cl_2$, transferred to a 500 ml dropping funnel and added dropwise to the biphenol/DMAP solution at 32° C. within one hour. The solution was stirred at room temperature overnight. The next morning, the solvent was removed under reduced pressure. The slightly waxy, reddish residue was admixed with 800 ml of n-heptane and stirred overnight. This gave a white residue which was filtered off, washed twice with 50 ml of n-heptane and then dried. The target product was obtained as a white solid (161.6 g, 84%). $^1$H-NMR (toluene-ds): 95% and further impurities.

Reaction of tert-butyl (3,3'-di-tert-butyl-2'-hydroxy-5,5'-dimethoxy-[1,1'-biphenyl]-2-yl)carbonate with phosphorus trichloride In a 250 ml Schlenk flask which had been repeatedly evacuated and filled with inert gas, 12 g (0.026 mol) of tert-butyl (3,3'-di-tert-butyl-2'-hydroxy-5,5'-dimethoxy-[1,1'-biphenyl]-2-yl)carbonate were dissolved by stirring in 120 ml of dried toluene and 12.8 ml (0.091 mol) of triethylamine.

In a second 500 ml Schlenk flask, 100 ml of dried toluene were first stirred together with 8.1 ml (0.091 mol) of phosphorus trichloride. Subsequently, the phosphorus trichloride-toluene solution was added dropwise to the previously prepared carbonate-amine-toluene solution at room temperature within 30 minutes. On completion of addition, the mixture was heated to 80° C. for 30 minutes and cooled to RT overnight.

The next morning, the mixture was filtered, the solids were washed with 50 ml of dried toluene, and the filtrate was concentrated to dryness. The target product was obtained as a solid (13.1 g, 89%). $^{31}$P NMR (202.4 MHz, toluene-ds): 203.2 and 203.3 ppm (100%).

Synthesis of L4

Reaction of tert-butyl (3,3'-di-tert-butyl-2'-((dichlorophosphino)oxy)-5,5'-dimethoxy-[1,1'-biphenyl]-2-yl)carbonate with 3,3,5,5-tetra-tert-butylbiphenyl

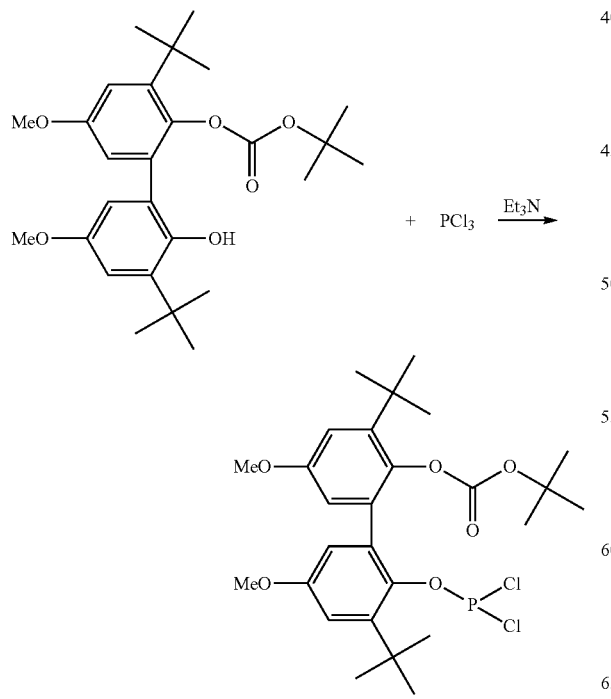

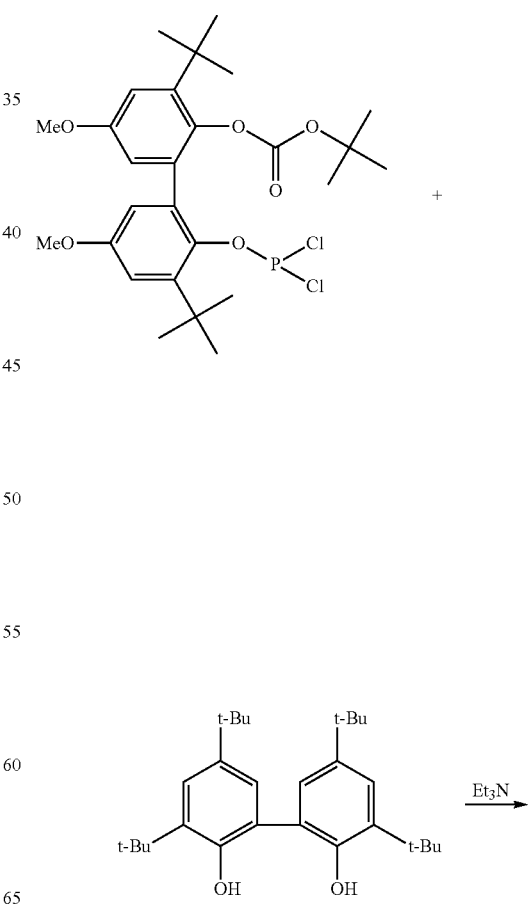

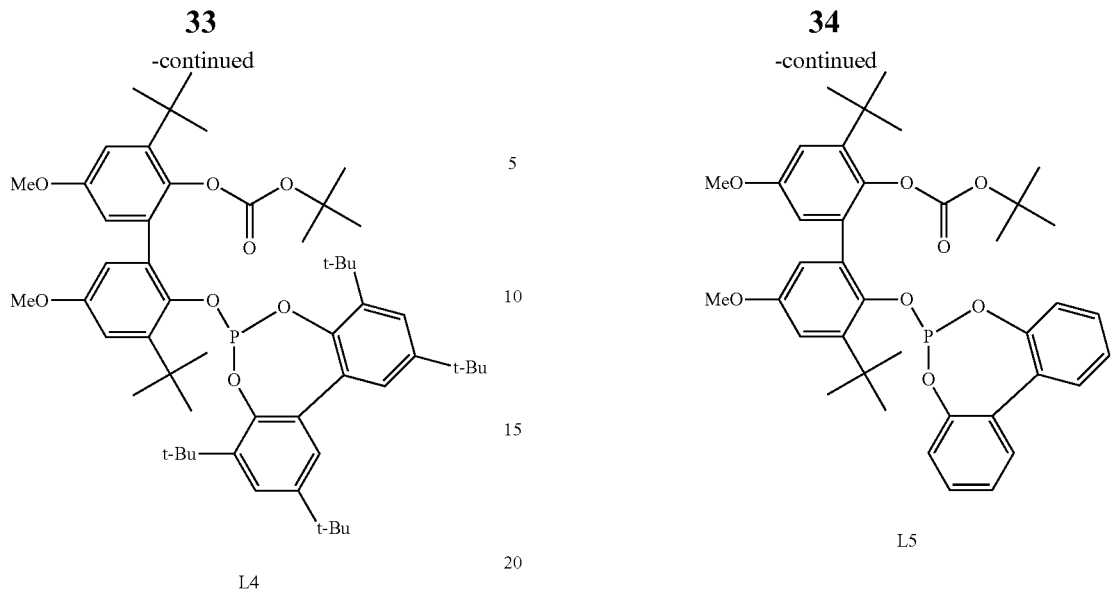

L4

In a 250 ml Schlenk flask which had been repeatedly evacuated and filled with inert gas, 7.0 g (0.0125 mol) of tert-butyl (3,3'-di-tert-butyl-2'-((dichlorophosphino)oxy)-5,5'-dimethoxy-[1,1'-biphenyl]-2-yl)carbonate were dissolved in 100 ml of dried acetonitrile.

In a second Schlenk flask (100 ml) which had been repeatedly evacuated and filled with inert gas, 5.1 g (0.0125 mol) of 3,3',5,5'-tetra-tert-butylbiphenol were dissolved in 60 ml of dried acetonitrile and 4.2 ml (0.03 mol) of dried triethylamine while stirring. Subsequently, the biphenol-triethylamine solution was slowly added dropwise at room temperature to the chlorophosphite solution and the mixture was stirred overnight. A portion of the solvent was removed under reduced pressure. The precipitated solids were filtered off and dried. The target product was obtained as a white solid (10.2 g, 91%). 31P NMR (202.4 MHz, toluene-d8): 142.7 ppm (100%).

Synthesis of L5

Reaction of tert-butyl (3,3'-di-tert-butyl-2'-((dichlorophosphino)oxy)-5,5'-dimethoxy-[1,1'-biphenyl]-2-yl)carbonate with 2,2'-biphenol

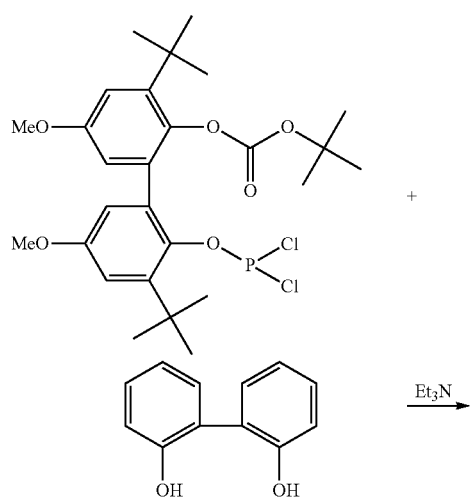

In a 250 ml Schlenk flask which had been repeatedly evacuated and filled with inert gas, 10.5 g (0.019 mol) of tert-butyl (3,3'-di-tert-butyl-2'-((dichlorophosphino)oxy)-5,5'-dimethoxy-[1,1'-biphenyl]-2-yl)carbonate were dissolved in 50 ml of degassed acetonitrile while stirring.

In a second Schlenk flask (250 ml) which had been repeatedly evacuated and filled with inert gas, 3.6 g (0.019 mol) of 2,2'-biphenol were dissolved in 40 ml of degassed acetonitrile and 6.3 ml (0.045 mol) of dried triethylamine while stirring. Subsequently, the chlorophosphite mixture was slowly added dropwise at room temperature to the biphenol/triethylamine solution, and the mixture was stirred at room temperature overnight. The resultant solids were filtered and dried. The target product was obtained as a white solid (11.5 g, 90%). $^{31}$P NMR (202.4 MHz, toluene-d8): 146.2 ppm (100%).

The inventive monophosphite compounds L1 to L3 and the comparative compounds L4 and L5 were each used for catalysis of hydroformylation reactions. The olefin used in each case was di-n-butene (a mixture of isomers of n-octenes (about 16%), 3-methylheptenes (about 65%) and 3,4-dimethylhexenes (about 19%)).

The reaction parameters and the yields achieved in each case are summarized in Table 1 below:

TABLE 1

Overview of the reaction parameters

| Compound | Synthesis gas pressure in [bar] | T in [° C.] | c(Rh) in ppm | P:Rh | Yield in % |
|---|---|---|---|---|---|
| L1* | 50 | 130 | 100 | 20 | 92 |
| L1* | 50 | 140 | 100 | 20 | 84 |
| L2* | 50 | 130 | 100 | 20 | 79 |
| L3* | 50 | 120 | 100 | 20 | 90 |
| L3* | 50 | 130 | 100 | 20 | 89 |
| L4 | 50 | 140 | 100 | 20 | 38 |
| L5 | 50 | 140 | 100 | 10 | 74 |

*inventive compound

As can be inferred from Table 1, the inventive compounds L1, L2 and L3 and the comparative compounds L4 and L5 were used for catalysis in hydroformylation reactions at a constant temperature in each case within the range from 120° C. to 140° C.

With all the compounds of the invention used, a good to very good yield was achieved, in each case above the yield achieved with the comparative compound L5 and well above the yield achieved with the comparative compound L4.

The compounds of the invention are therefore notable for very good suitability for catalysis and are thus of very good suitability as catalysts for the hydroformylation reaction of technical olefin mixtures.

The invention claimed is:

1. Compound having one of the two general structures I and II:

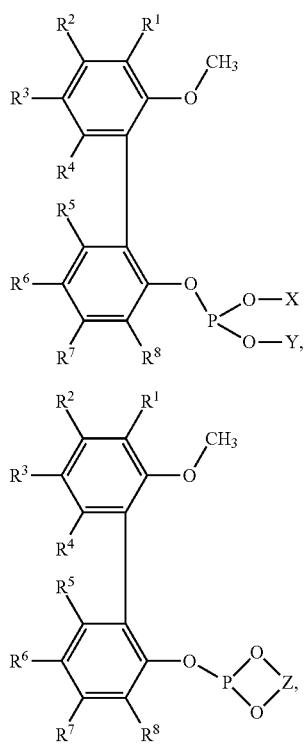

where $R^1$, $R^2$, $R^3$, $R^4$, $R^5$, $R^6$, $R^7$, $R^8$ are each independently selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —Cl, —F, —Br, —I, —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, —N[($C_1$-$C_{12}$)-alkyl]$_2$;

where X and Y are each independently selected from:
—($C_1$-$C_{12}$)-alkyl, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_1$-$C_{12}$)-alkyl-($C_6$-$C_{20}$)-aryl, —($C_6$-$C_{20}$)-aryl-COO—($C_1$-$C_{12}$)-alkyl, —($C_6$-$C_{20}$)-aryl-CONH—($C_1$-$C_{12}$)-alkyl, —($C_6$-$C_{20}$)-aryl-CON[($C_1$-$C_{12}$)-alkyl]$_2$, —($C_4$-$C_{20}$)-heteroaryl, —($C_4$-$C_{20}$)-heteroaryl-($C_1$-$C_{12}$)-alkyl, —($C_5$-$C_8$)-cycloalkyl, —($C_5$-$C_8$)-heterocycloalkyl, —($C_6$-$C_{20}$)-aryl-CO—($C_6$-$C_{20}$)-aryl;

where Z is selected from:
—($C_1$-$C_{12}$)-alkyl, —($C_6$-$C_{20}$)-aryl, —($C_6$-$C_{20}$)-aryl-($C_1$-$C_{12}$)-alkyl, —($C_1$-$C_{12}$)-alkyl-O—($C_6$-$C_{20}$)-aryl, —($C_4$-$C_{20}$)-heteroaryl-, —($C_6$-$C_{20}$)-aryl-CO—($C_6$-$C_{20}$)-aryl-, —($C_6$-$C_{20}$)-aryl-($C_6$-$C_{20}$)-aryl-;

and where the alkyl, heteroalkyl, cycloalkyl, heterocycloalkyl, aryl and heteroaryl groups mentioned may be substituted.

2. Compound according to claim 1,
where X and Y are each independently selected from:
—($C_1$-$C_{12}$)-alkyl-, —($C_6$-$C_{20}$)-aryl-, —($C_6$-$C_{20}$)-aryl-($C_1$-$C_{12}$)-alkyl-, —($C_1$-$C_{12}$)-alkyl-($C_6$-$C_{20}$)-aryl-, —($C_4$-$C_{20}$)-heteroaryl and —($C_5$-$C_8$)-cycloalkyl.

3. Compound according to claim 1,
where Z is selected from:
—($C_1$-$C_{12}$)-alkyl-, —($C_6$-$C_{20}$)-aryl-, —($C_6$-$C_{20}$)-aryl-($C_1$-$C_{12}$)-alkyl-, —($C_1$-$C_{12}$)-alkyl-($C_6$-$C_{20}$)-aryl- and —($C_6$-$C_{20}$)-aryl-($C_6$-$C_{20}$)-aryl-.

4. Compound according to claim 1, wherein X and Y are the same radicals.

5. Compound according to claim 1, having the general structure III:

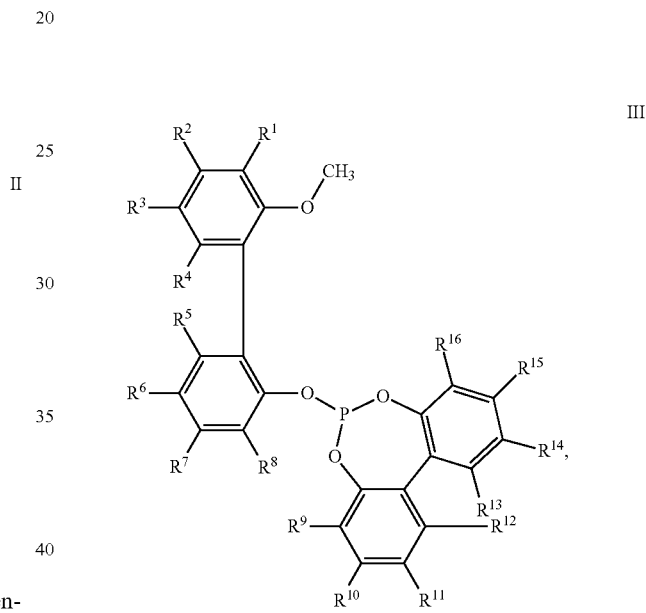

where $R^1$, $R^2$, $R^3$, $R^4$, $R^5$, $R^6$, $R^7$, $R^8$ are each independently selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —Cl, —F, —Br, —I, —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, —N[($C_1$-$C_{12}$)-alkyl]$_2$;

and where $R^9$, $R^{10}$, $R^{11}$, $R^{12}$, $R^{13}$, $R^{14}$, $R^{15}$, $R^{16}$ are each independently selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —Cl, —F, —Br, —I, COO—($C_1$-$C_{12}$)-alkyl, CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, —N[($C_1$-$C_{12}$)-alkyl]$_2$.

6. Compound according to claim 1, wherein the compound has a structure selected from L1, L2 and L3:

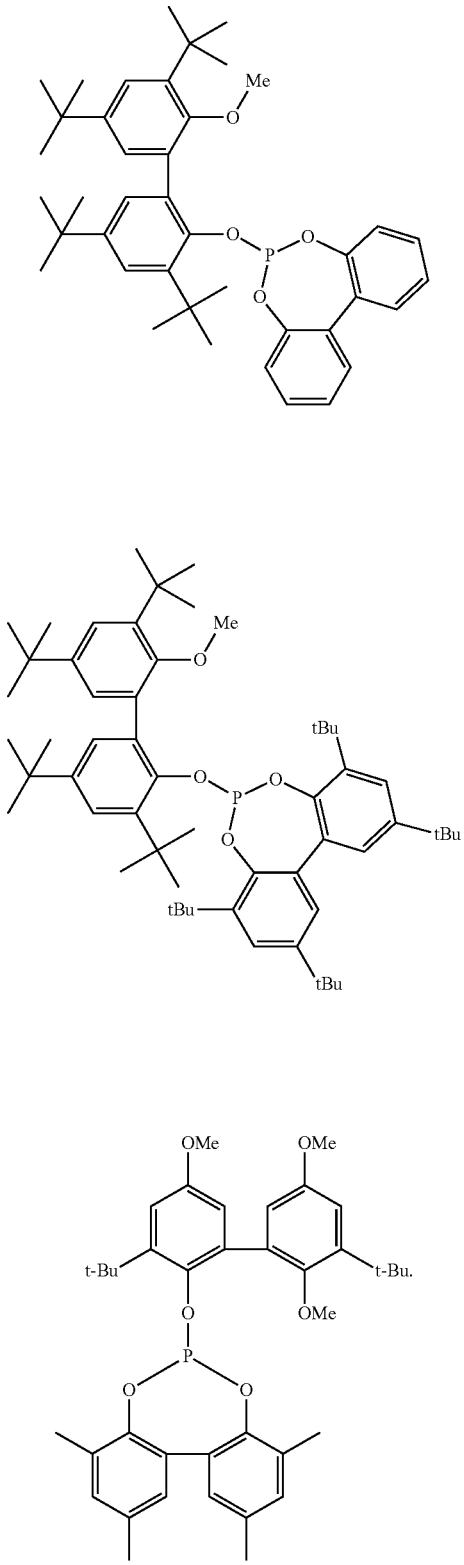

7. Process for preparing a compound having one of the two general structures I and II:

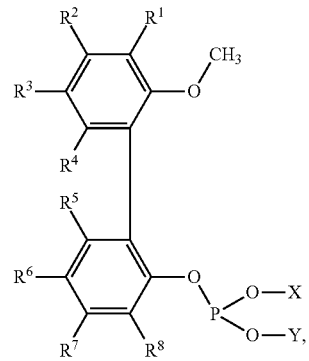

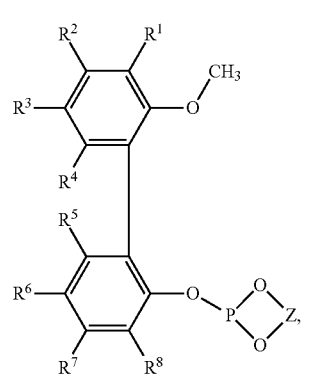

where $R^1$, $R^2$, $R^3$, $R^4$, $R^5$, $R^6$, $R^7$, $R^8$ are each independently selected from:

—H, —$(C_1\text{-}C_{12})$-alkyl, —O—$(C_1\text{-}C_{12})$-alkyl, —O—$(C_6\text{-}C_{20})$-aryl, —$(C_6\text{-}C_{20})$-aryl, —Cl, —F, —Br, —I, —COO—$(C_1\text{-}C_{12})$- alkyl, —CONH—$(C_1\text{-}C_{12})$-alkyl, —$(C_6\text{-}C_{20})$-aryl-CON[$(C_1\text{-}C_{12})$-alkyl]$_2$, —CO—$(C_1\text{-}C_{12})$-alkyl, —CO—$(C_6\text{-}C_{20})$-aryl, —COOH, —OH, —$SO_3H$, —$SO_3Na$, —$NO_2$, —CN, —$NH_2$, —N[$(C_1\text{-}C_{12})$-alkyl]$_2$;

where X and Y are each independently selected from:

—$(C_1\text{-}C_{12})$-alkyl, —$(C_6\text{-}C_{20})$-aryl, —$(C_6\text{-}C_{20})$-aryl-$(C_1\text{-}C_{12})$-alkyl, —$(C_6\text{-}C_{20})$-aryl-O—$(C_1\text{-}C_{12})$-alkyl, —$(C_1\text{-}C_{12})$-alkyl-$(C_6\text{-}C_{20})$-aryl, —$(C_6\text{-}C_{20})$-aryl-COO—$(C_1\text{-}C_{12})$-alkyl, —$(C_6\text{-}C_{20})$-aryl-CONH—$(C_1\text{-}C_{12})$-alkyl, —$(C_6\text{-}C_{20})$-aryl-CON[$(C_1\text{-}C_{12})$-alkyl]$_2$, —$(C_4\text{-}C_{20})$-heteroaryl, —$(C_4\text{-}C_{20})$-heteroaryl-$(C_1\text{-}C_{12})$-alkyl, —$(C_5\text{-}C_8)$-cycloalkyl, —$(C_5\text{-}C_8)$-heterocycloalkyl, —$(C_6\text{-}C_{20})$-aryl-CO—$(C_6\text{-}C_{20})$-aryl;

and where Z is selected from:

—$(C_1\text{-}C_{12})$-alkyl, —$(C_6\text{-}C_{20})$-aryl, —$(C_6\text{-}C_{20})$-aryl-$(C_1\text{-}C_{12})$-alkyl, —$(C_1\text{-}C_{12})$-alkyl-O—$(C_6\text{-}C_{20})$-aryl, —$(C_4\text{-}C_{20})$-heteroaryl-, —$(C_6\text{-}C_{20})$-aryl-CO—$(C_6\text{-}C_{20})$-aryl-, —$(C_6\text{-}C_{20})$-aryl-$(C_6\text{-}C_{20})$-aryl-;

where the process comprises the following steps:

a) initially charging a reactant, b) adding a methylating reagent, c) adding a compound containing phosphorus and chlorine, d) obtaining a product.

8. Process according to claim 7, wherein an intermediate having a structure of formula 40 is formed

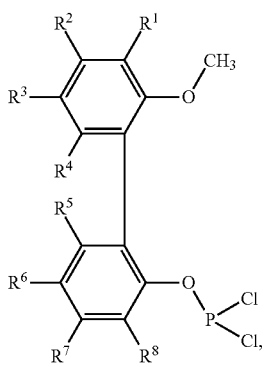

where $R^1$, $R^2$, $R^3$, $R^4$, $R^5$, $R^6$, $R^7$, $R^8$ are each independently selected from:

—H, —$(C_1\text{-}C_{12})$-alkyl, —O—$(C_1\text{-}C_{12})$-alkyl, —O—$(C_6\text{-}C_{20})$-aryl, —$(C_6\text{-}C_{20})$-aryl, —Cl, —F, —Br, —I, —COO—$(C_1\text{-}C_{12})$-alkyl, —CONH—$(C_1\text{-}C_{12})$-alkyl, —$(C_6\text{-}C_{20})$-aryl-CON[$(C_1\text{-}C_{12})$-alkyl]$_2$, —CO—$(C_1\text{-}C_{12})$-alkyl, —CO—$(C_6\text{-}C_{20})$-aryl, —COOH, —OH, —SO$_3$H, —SO$_3$Na, —NO$_2$, —CN, —NH$_2$, —N[$(C_1\text{-}C_{12})$-alkyl]$_2$.

9. Process according to claim 7, wherein the reactant used is a compound having a structure of formula 20

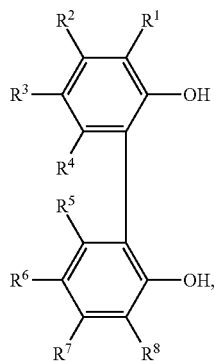

where $R^1$, $R^2$, $R^3$, $R^4$, $R^5$, $R^6$, $R^7$, $R^8$ are each independently selected from:

—H, —$(C_1\text{-}C_{12})$-alkyl, —O—$(C_1\text{-}C_{12})$-alkyl, —O—$(C_6\text{-}C_{20})$-aryl, —$(C_6\text{-}C_{20})$-aryl, —Cl, —F, —Br, —I, —COO—$(C_1\text{-}C_{12})$-alkyl, —CONH—$(C_1\text{-}C_{12})$-alkyl, —$(C_6\text{-}C_{20})$-aryl-CON[$(C_1\text{-}C_{12})$-alkyl]$_2$, —CO—$(C_1\text{-}C_{12})$-alkyl, —CO—$(C_6\text{-}C_{20})$-aryl, —COOH, —OH, —SO$_3$H, —SO$_3$Na, —NO$_2$, —CN, —NH$_2$, —N[$(C_1\text{-}C_{12})$-alkyl]$_2$;

and wherein the compound containing phosphorus and chlorine is a chlorophosphite having a structure of formula 50

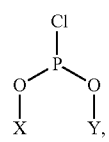

where X and Y are each independently selected from:

—$(C_1\text{-}C_{12})$-alkyl, —$(C_6\text{-}C_{20})$-aryl, —$(C_6\text{-}C_{20})$-aryl-$(C_1\text{-}C_{12})$-alkyl, —$(C_6\text{-}C_{20})$-aryl-O—$(C_1\text{-}C_{12})$-alkyl, —$(C_1\text{-}C_{12})$-alkyl-$(C_6\text{-}C_{20})$-aryl, —$(C_6\text{-}C_{20})$-aryl-COO—$(C_1\text{-}C_{12})$-alkyl, —$(C_6\text{-}C_{20})$-aryl-CONH—$(C_1\text{-}C_{12})$-alkyl, —$(C_6\text{-}C_{20})$-aryl-CON[$(C_1\text{-}C_{12})$-alkyl]$_2$, —$(C_4\text{-}C_{20})$-heteroaryl, —$(C_4\text{-}C_{20})$-heteroaryl-$(C_1\text{-}C_{12})$-alkyl, —$(C_5\text{-}C_8)$-cycloalkyl, —$(C_5\text{-}C_8)$-heterocycloalkyl, —$(C_6\text{-}C_{20})$-aryl-CO—$(C_6\text{-}C_{20})$-aryl.

10. Process according to claim 7, wherein the reactant used is a compound having a structure of formula 20

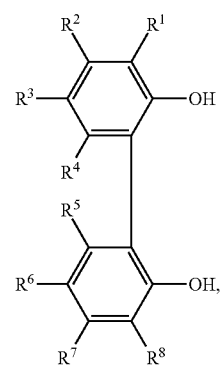

where $R^1$, $R^2$, $R^3$, $R^4$, $R^5$, $R^6$, $R^7$, $R^8$ are each independently selected from:

—H, —$(C_1\text{-}C_{12})$-alkyl, —O—$(C_1\text{-}C_{12})$-alkyl, —O—$(C_6\text{-}C_{20})$-aryl, —$(C_6\text{-}C_{20})$-aryl, —Cl, —F, —Br, —I, —COO—$(C_1\text{-}C_{12})$-alkyl, —CONH—$(C_1\text{-}C_{12})$-alkyl, —$(C_6\text{-}C_{20})$-aryl-CON[$(C_1\text{-}C_{12})$-alkyl]$_2$, —CO—$(C_1\text{-}C_{12})$-alkyl, —CO—$(C_6\text{-}C_{20})$-aryl, —COOH, —OH, —SO$_3$H, —SO$_3$Na, —NO$_2$, —CN, —NH$_2$, —N[$(C_1\text{-}C_{12})$-alkyl]$_2$;

and wherein the compound containing phosphorus and chlorine is a chlorophosphite having a structure of formula 60

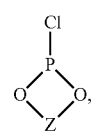

where Z is selected from:

—$(C_1\text{-}C_{12})$-alkyl, —$(C_6\text{-}C_{20})$-aryl, —$(C_6\text{-}C_{20})$-aryl-$(C_1\text{-}C_{12})$-alkyl, —$(C_1\text{-}C_{12})$-alkyl-O—$(C_6\text{-}C_{20})$-aryl, —$(C_4\text{-}C_{20})$-heteroaryl-, —$(C_6\text{-}C_{20})$-aryl-CO—$(C_6\text{-}C_{20})$-aryl-, —$(C_6\text{-}C_{20})$-aryl-$(C_6\text{-}C_{20})$-aryl-.

11. Process according to claim 7, wherein an intermediate having a structure of formula 30 is formed

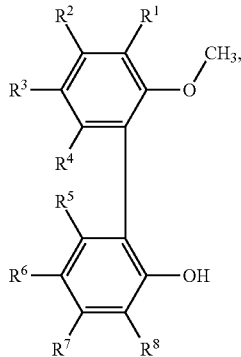

where $R^1$, $R^2$, $R^3$, $R^4$, $R^5$, $R^6$, $R^7$, $R^8$ are each independently selected from:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —Cl, —F, —Br, —I, —COO—($C_1$-$C_{12}$)- alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, —N[($C_1$-$C_{12}$)-alkyl]$_2$.

12. Complex comprising a metal atom or ion and at least one compound according to claim 1.

13. Complex according to claim 12, wherein the metal atom or ion is selected from the group comprising Rh, Ru, Co and Ir.

14. A process for the hydroformylation of ($C_2$-$C_{24}$) olefins, comprising: introducing a compound having one of the two general structures I and II:

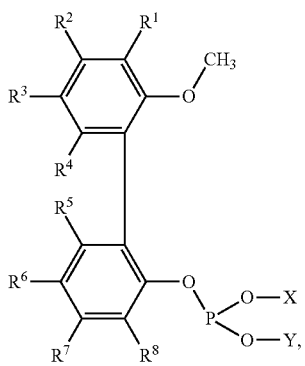

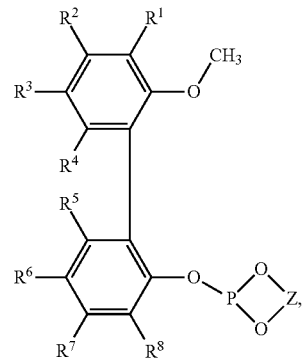

where $R^1$, $R^2$, $R^3$, $R^4$, $R^5$, $R^6$, $R^7$, $R^8$ are each independently selected from:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —Cl, —F, —Br, —I, —COO—($C_1$-$C_{12}$)- alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_9$, —CN, —NH$_9$, —N[($C_1$-$C_{12}$)-alkyl]$_2$;

where X and Y are each independently selected from:

—($C_1$-$C_{12}$)-alkyl, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_1$-$C_{12}$)-alkyl-($C_6$-$C_{20}$)-aryl, —($C_6$-$C_{20}$)-aryl-COO—($C_1$-$C_{12}$)-alkyl, —($C_6$-$C_{20}$)-aryl-CONH—($C_1$-$C_{12}$)-alkyl, —($C_6$-$C_{20}$)-aryl-CON[($C_1$-$C_{12}$)-alkyl]$_2$, —($C_4$-$C_{20}$)-heteroaryl, —($C_4$-$C_{20}$)-heteroaryl-($C_1$-$C_{12}$)-alkyl, —($C_5$-$C_8$)-cycloalkyl, —($C_5$-$C_8$)-heterocycloalkyl, —($C_6$-$C_{20}$)-aryl-CO—($C_6$-$C_{20}$)-aryl;

where Z is selected from:

—($C_1$-$C_{12}$)-alkyl, —($C_6$-$C_{20}$)-aryl, —($C_6$-$C_{20}$)-aryl-($C_1$-$C_{12}$)-alkyl, —($C_1$-$C_{12}$)-alkyl-O—($C_6$-$C_{20}$)-aryl, —($C_4$-$C_{20}$)-heteroaryl-, —($C_6$-$C_{20}$)-aryl-CO—($C_6$-$C_{20}$)-aryl-, —($C_6$-$C_{20}$)-aryl-($C_6$-$C_{20}$)-aryl-;

and where the alkyl, heteroalkyl, cycloalkyl, heterocycloalkyl, aryl and heteroaryl groups mentioned may be substituted;

or a complex according to claim 12.

15. Process according to claim 14, wherein the hydroformylation reaction comprises the following steps:

a) initially charging an olefin, b) adding said complex,
   or said compound and a compound containing a metal atom or metal ion, c) feeding in H$_2$ and CO, d) heating the reaction mixture, with conversion of the olefin to an aldehyde.

16. Compound according to claim 5, wherein the compound has a structure selected from L1, L2 and L3:
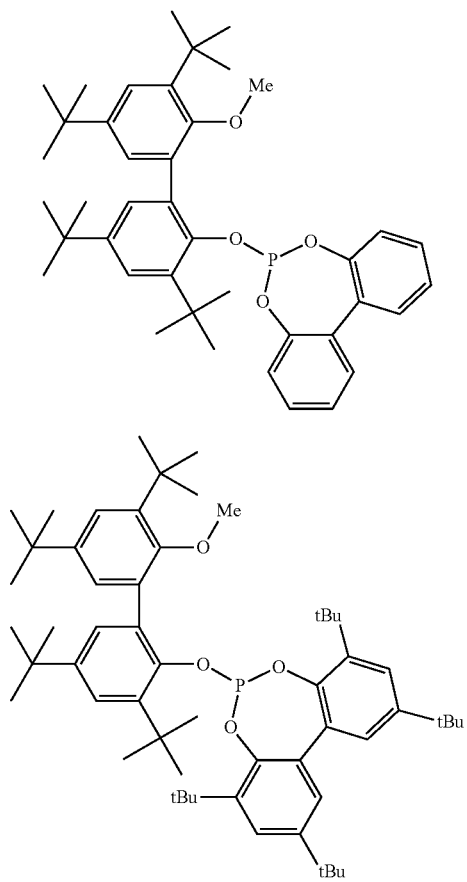
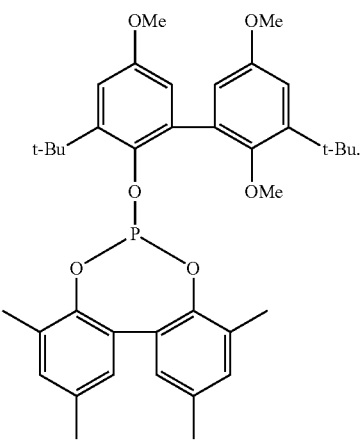
17. Complex comprising a metal atom or ion and at least one compound according to claim 5.
18. Complex according to claim 17, wherein the metal atom or ion is selected from the group comprising Rh, Ru, Co and Ir.
* * * * *